US006194141B1

United States Patent

(12) United States Patent
Paul et al.

(10) Patent No.: US 6,194,141 B1
(45) Date of Patent: Feb. 27, 2001

(54) INHIBITION OF PICORNAVIRUS GENOME REPLICATION BY INTERFERENCE WITH VPG-NUCLEOTIDYLYLATION AND ELONGATION

(75) Inventors: Aniko V. Paul, Setauket; Eckard Wimmer, E. Setauket; Elizabeth Rieder, Port Jefferson Station, all of NY (US)

(73) Assignee: The Research Foundation of State University of New York, Albany, NY (US)

(*) Notice: Subject to any disclaimer, the term of this patent is extended or adjusted under 35 U.S.C. 154(b) by 0 days.

(21) Appl. No.: 09/282,351

(22) Filed: Mar. 31, 1999

Related U.S. Application Data

(60) Provisional application No. 60/080,161, filed on Mar. 31, 1998.

(51) Int. Cl.[7] .......... C12Q 1/00; C12Q 1/68
(52) U.S. Cl. .......... 435/4; 435/6
(58) Field of Search .......... 435/4, 5, 6

(56) References Cited

PUBLICATIONS

Ambros, V., et al., (1978), "Protein Is Linked to the 5' End of Poliovirus RNA by a Phosphodiester Linkage to Tyrosine", *The Journal of Biological Chemistry,* 253(15):5263–5266.

Barton, D. J., et al., (1996), "Poliovirus RNA Polymerase Mutation 3D–M394T Results in a Temperature–Sensitive Defect in RNA Synthesis", *Virology 217,* Article No. 0140:459–469.

Blanco, L., et al., (1985), "Replication of phage ϕ29 DNA with purified terminal protein and DNA polymerase: Synthesis of full–length ϕ29 DNA", *Biochemistry,* 82:6404–6408.

Cao, X., et al., (1995), "Intragenomic Complementation of a 3AB Mutant in Dicistronic Polioviruses", *Virology,* 209:315–326.

Dobos, P., (1995), "Protein–Primed RNA Synthesis in Vitro by the Virion–Associated RNA Polymerase of Infectious Pancreatic Necrosis Virus", *Virology,* 208:19–25.

Dorsch–Häsler, K., et al., (1975), "Replication of Picornaviruses", *Journal of Virology,* 16(6):1512–1527.

Dreef–Tromp, C. M., et al., (1992), "Solid–phase synthesis of an RNA nucleopeptide fragment from the nucleoprotein of poliovirus", *Nucleic Acids Research,* 20(10):2435–2439.

Esteban, J. A., et al., (1992), "Metal Activation of Synthetic and Degradative Activities of ϕ29 DNA Polymerase, a Model Enzyme for Protein–Primed DNA Replication", *Biochemistry,* 31:350–359.

Flanegan, J. B., et al., (1977), "Covalent linkage of a protein to a defined nucleotide sequence at the 5'–terminus of virion and replicative intermediate RNAs of poliovirus", *Biochemistry,* 74(3):961–965.

Flanegan, J. B., et al. (1977), "Poliovirus–specific primer–dependent RNA polymerase able to copy poly(A)", *Biochemistry,* 74(9):3677–3680.

Hsieh, J., et al., (1990), "An essential arginine residue for initiation of protein–primed DNA replication", *Biochemistry,* 87:8665–8669.

Jang, S. K., et al., (1988), "A Segment of the 5' Nontranslated Region of Encephalomyocarditis Virus RNA Directs Internal Entry of Ribosomes during In Vitro Translation", *Journal of Virology,* 62(8):2636–2643.

Kitamura, N., et al., (1981), "Primary structure, gene organization and polypeptide expression of poliovirus RNA", *Nature,* 291:547–553.

Kuhn, R. J., et al., (1988), "Construction of a "mutagenesis cartridge" for poliovirus genome–linked viral protein: Isolation and characterization of viable and nonviable mutants", *Genetics,* 85:519–523.

Lee Y. F., et al., (1977), "A protein covalently linked to poliovirus genome RNA", *Biochemistry,* 84(1):59–62.

Lee, Y. F., et al., "The Genome of Poliovirus Is an Exceptional Eukaryotic mRNA", *Dept. of Microbiology, School of Basic Health Sciences,* pp. 89–96. Prog. Nucleic Acid Res. Mol. Biol. (1976) 19:89–96.

Molla, A., et al., (1992), "Cardioviral internal ribosomal entry site is functional in a genetically engineered dicistronic poliovirus", *Nature,* 356:255–257.

Nomoto, A., et al., (1977), The location of the polio genome protein in viral RNAs and its implication for RNA synthesis, *Nature,* 268:208–213.

Pata, J. D., et al., (1995), "Functional oligomerization of poliovirus RNA–dependent RNA polymerase", RNA, 1:466–477.

Paul, A. V., et al., (1998), "Protein–primed RNA synthesis by purified poliovirus RNA polymerase", *Nature,* 393:280–284.

Paul, A. V., et al., (1994), "Studies with Poliovirus Polymerase $3D^{pol}$", *The Journal of Biological Chemistry,* 269(46):29173–29181.

(List continued on next page.)

*Primary Examiner*—Robert A. Schwartzman
(74) *Attorney, Agent, or Firm*—Scully, Scott, Murphy & Presser

(57) ABSTRACT

The present invention provides methods of inhibiting picornavirus genome replication in a subject. In particular, methods for interfering with VPg uridylylation and elongation are provided. The methods comprise administering to a subject an effective amount of at least one of VPg, VPg analog, VPg homology or biologically active fragment thereof as well as oligonucleotides, divalent cations, ribonucleotide or deoxyribonucleotide. Also provided are methods of identifying an inhibitor of picornaviral replication which comprise adding a potential inhibitor of picornaviral replication to an in vitro assay and analyzing levels of VPg uridylylation reaction products.

13 Claims, 14 Drawing Sheets

OTHER PUBLICATIONS

Figure 1A:
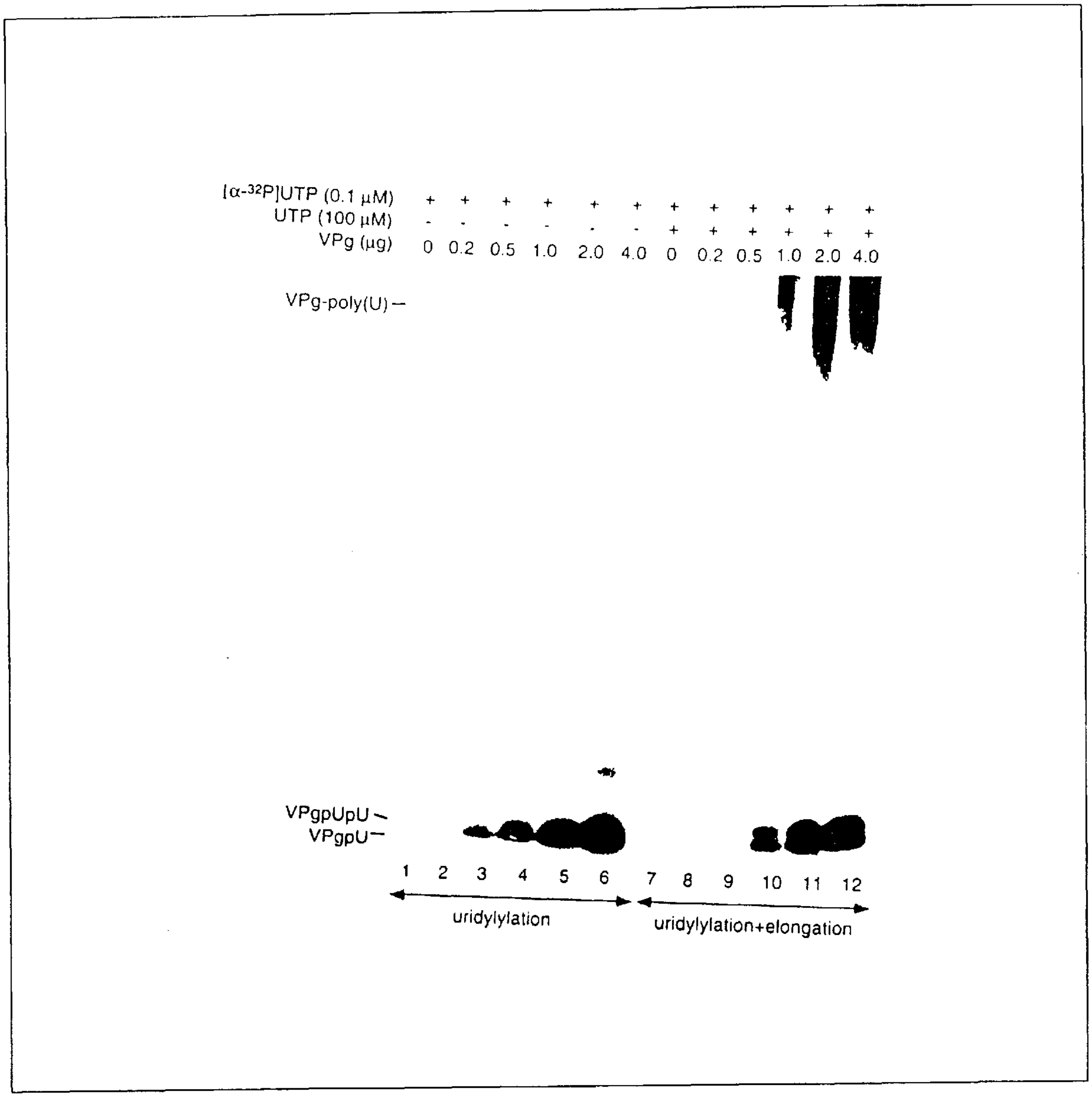

Pelletier, J., et al., (1988), "Internal initiation of translation of eukaryotic mRNA directed by a sequence derived from poliovirus RNA", *Nature,* 334:320–325.

Richards, O. C., et al., (1990), "Poliovirus RNA Replication", *Current Topics in Microbiology and Immunology,* 161:90–119.

Rodriguez, P. L., et al, (1992), "Gliotoxin: Inhibitor of Poliovirus RNA Synthesis That Blocks the Viral RNA Polymerase $3D^{pol}$", *Journal of Virology,* 66(4):1971–1976.

Rothberg, P. G., et al., (1978), "$O^4$–(5'–Uridylyl)tyrosine is the bond between the genome–linked protein and the RNA of poliovirus", *Biochemistry,* 75(10):4868–4872.

Salas, M., (1991), "Protein–Priming of DNA Replication", *Annu. Rev. Biochem.,* 60:39–71.

Takeda, N., et al., (1986), "Initiation of Poliovirus Plus–Strand RNA Synthesis in a Membrane Complex of Infected HeLa Cells", *Journal of Virology,* 60(1):43–53.

Takeda, N., et al., (1987), "Uridylylation of the genome–linked protein of poliovirus in vitro is dependent upon an endogenous RNA template", *Virus Research,* 8:193–204.

Takegami, T., et al., (1983), "Membrane–dependent uridylylation of the genome–linked protein VPg of poliovirus", *Biochemistry,* 80:7447–7451.

Toyoda, H., et al., (1987), "Analysis of RNA Synthesis of Type 1 Poliovirus by Using an In Vitro Molecular Genetic Approach", *Journal of Virology,* 61(9):2816–2822.

Vartapetian, A. B., et al., (1984), "Encephalomyocarditis virus RNA synthesis in vitro is protein–primed", *The EMBO Journal,* 3(11):2593–2598.

Wimmer, E., (1982), "Genome–Linked Proteins of Viruses", *Cell,* 28:199–201.

Xiang, W., et al., (1995), "Molecular dissection of the multifunctional poliovirus NRA–binding protein 3AB", RNA, 1:892–904.

Yogo, Y., et al., (1972), "Polyadenylic Acid at the 3'–Terminus of Poliovirus RNA", *Proc. Nat. Acad. Sci.,* 69(7):1877–1882.

Yogo, Y., et al., (1975), "Sequence Studies of Poliovirus RNA", *J. Mol. Biol.,* 92:467–477.

| Genotype | VPg | Growth |
|---|---|---|
| | 1    5    10   15   20 | |
| wt | G A Y T G L P N K K P N V P T I R T A K V Q | + + + |
| Y3F | - - F - - - - - - - - - - - - - - - - - - | - * |
| T4A | - - - A - - - - - - - - - - - - - - - - - | + + |
| R17E | - - - - - - - - - - - - - - - - E - - - - | - |

* quasi-infectious

Schematic representation of PVcre(2C)wt and mutants

<u>4435-4502 Stem-loop 2C</u>

```
                         G
[PVcre(2C) M2]          ↖
                       A   C   A
                      A        C
                      A        C
                      C  G
                      G  U
                     A       A
                    G A  U
                      A  U
                   U ← C  G
[PVcre(2C) M1]        U  A → G  [PVcre(2C) M3]
                      U  A
                   A ← G  C
                     A      C
                      C  G   A
                      A  U
                      U  A → U
                      A  U       [PVcre(2C) M4]
                      C  G
                    U A  U → C
                    C A  U
                      A  U ← 4497
                      C  G
                    A      C
                      A  U
                  A  U  U  A
                 U          G
                C
                 A
                  U A  C  G G
                      G  C
                    A        U
                      G  C
                         ↑
                       4435
```

Uridylylation of VPg on *wt* and mutant cre(2C) templates

Uridylylation of VPg on the cre(2C) template and stimulation of the reaction by 3CDpro

INHIBITION OF PICORNAVIRUS GENOME REPLICATION BY INTERFERENCE WITH VPG-NUCLEOTIDYLYLATION AND ELONGATION

This application claims priority from U.S. Provisional Application No. 60/080,161, filed on Mar. 31, 1998. This invention was made with United States government support under grants from the National Institute of Allergy and Infectious Diseases of the National Institutes of Health. The Unites States government may have certain rights in the invention.

BACKGROUND OF THE INVENTION

Single stranded RNA viruses are unique in having an RNA template which directs the biosynthesis of RNA. Upon infection of a cell, the genome of positive strand RNA viruses directs the synthesis of viral proteins which are required for the replication of the RNA. During the replication process, a negative strand RNA molecule is first produced followed by a subsequent transcription of the negative strand to produce new copies of the positive strand RNA. Richards, O. C. et al., (1990) *Current Topics in Microbiol. and Immun*. 161:89–119.

Despite the fact that RNA synthesis has been studied for the past thirty years or so in single stranded RNA viruses such as poliovirus, the biochemistry of single stranded RNA virus replication has not been clearly elucidated. Richards O. C. et al., 1990. Complicating the replication process is the finding that two groups of animal viruses (picornavirus and calicivirus) and five groups of plant viruses (comovirus, luteovirus, nepovirus, potyvirus, and sobemovirus) have been shown to contain a genome-linked viral protein (VPg) attached to the 5'-end of the single-stranded genome RNA. Salas, M. (1991) *Annu. Rev. Biochem*. 60: 39–71. See Table 3, taken from Salas, M., (1991). For example, poliovirus and encephalomyocarditis virus (EMCV), although polyadenylated at their 3' ends, are not conventionally capped at their 5' ends. Instead of having a 7-methyl guanosine triphosphate group, the RNAs are covalently linked to a VPg. Poliovirus-specific mRNA, however, isolated from infected cells lack VPg. HeLa cell extracts and rabbit reticulocyte lysates contain an enzyme activity that cleaves VPg from the 5' terminus of picornavirus RNA in vitro. It is thought that this activity modifies all newly synthesized viral RNAs destined to become mRNAs in vivo. Jang, S. K., et al., (1988) *J. Virol*. 62(8):2636–2643.

Picornaviridae are a large family of non-enveloped, positive-sense RNA animal viruses, comprised of six genera (Enterovirus, Parechovirus, Rhinovirus, Hepatovirus, Cardiovirus, and Aphthovirus) that contain numerous viral species (more than 200) known to cause important diseases of humans and animals, including type A viral hepatitis, aseptic meningitis, chronic heart disease and the common cold. Table 2. VPg proteins in picornaviruses are between 20 to 26 amino acids in length. Salas, 1991. In poliovirus, VPg is a protein of only 22 amino acids (Kitamura, N., et al. (1981) *Nature* 291, 547–553.) whose single tyrosine residue provides the link to the 5'-terminal uridylylic acid of the genome. Rothberg, P. G., et al. (1978) *Proc. Natl. Acad. Sci. USA* 75, 4868–4872. Ambros, V., et al. (1978) *J. Biol. Chem* 253, 5263–5266. Biochemical and genetic data have implicated protein(s) mapping to the 3D region of the viral polyprotein, in the formation of the $O^4$-(5'-uridylyl)tyrosine bond. (Takegami, T., et al. (1983) *Proc. Natl. Acad. Sci. USA* 80, 7447–7451; Takeda, N., et al. (1986) *J. Virol*. 60, 43–53; Toyoda, H., et al. (1987) *J. Virol*. 61, 2816–2822.

The precise role of VPg linked to the 5'-end of single stranded RNA viruses has not been clearly understood heretofore. In poliovirus, for example, the finding of VPg covalently linked to the 5'-end of poliovirus RNA, to nascent strands of poliovirus replicative intermediates, and to the poly(U) of minus strands, suggests that VPg serves as a primer for both the plus and minus strands of poliovirus RNA. Other findings suggest that a VPg precursor or a uridylylated form of VPg serves as a primer. Still another model suggests that a hairpin formed at the 3'-end of poliovirus RNA acts as a primer for minus-strand synthesis by the RNA polymerase. Salas, M. (1991).

Figure 7:
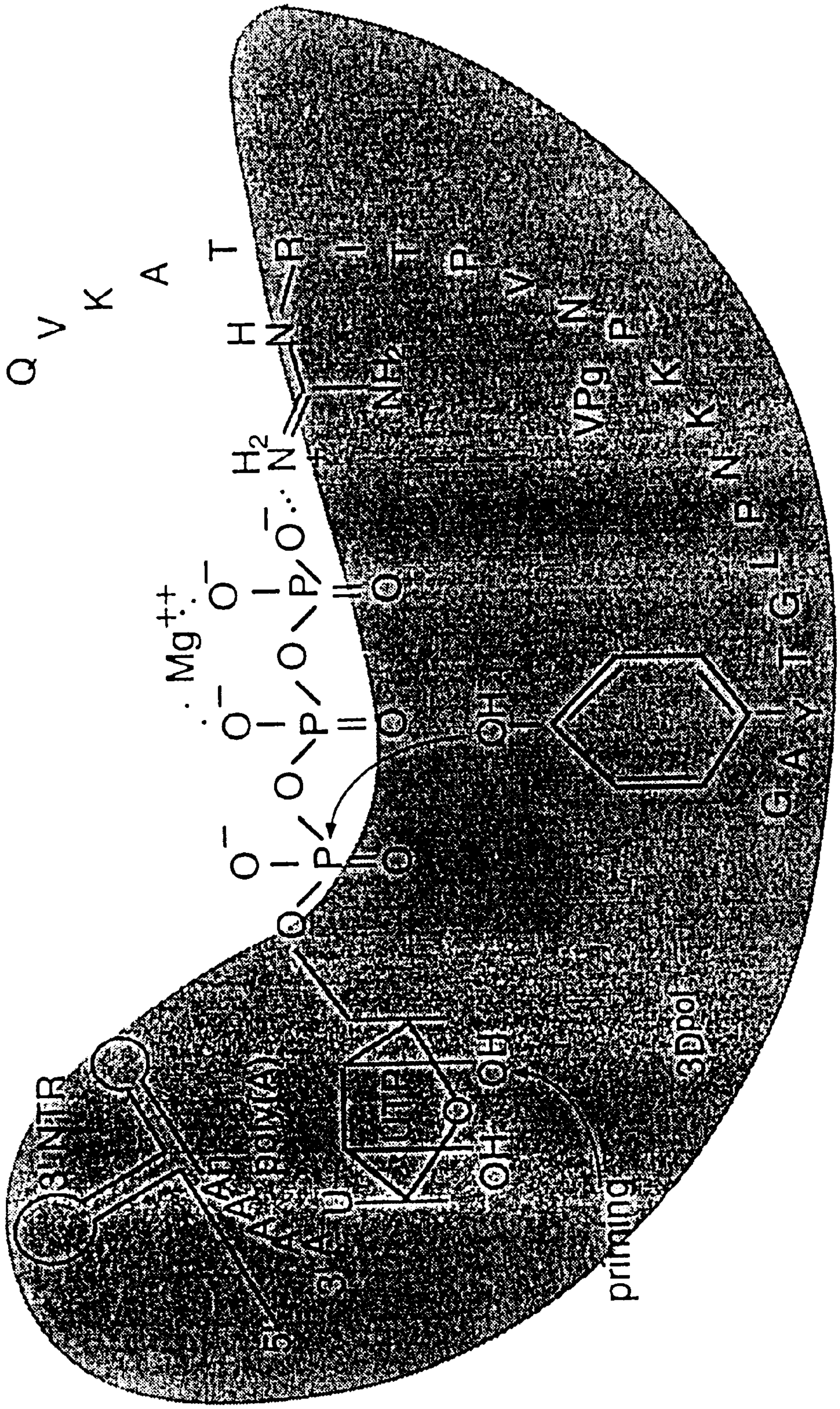

In accordance with the present invention, it has been surprisingly found that VPg, $3D^{pol}$, poly(A) and UTP form a complex that facilitates transfer of UMP to the hydroxyl of Y3 of VPg. Transcription of a poly(A) template is then initiated at the 3' hydroxyl group of UMP (FIG. 7, arrow). Knowledge of the biochemistry of picornavirus replication allows for intervention with various compositions in order to inhibit such replication. Inhibition of replication is especially valuable in preventing and ameliorating the progression of disease caused by picornaviruses.

SUMMARY OF THE INVENTION

The present invention provides methods of inhibiting picornavirus genome replication. In particular, methods for interfering with VPg-nucleotidylylation and elongation are provided.

In one embodiment of the invention, an effective amount of VPg, VPg analog, VPg homolog or a biologically active fragment thereof is administered to a subject in order to inhibit picornavirus genome replication. In this embodiment, the VPg, VPg analog, VPg homolog or biologically active fragment thereof competitively binds to the $3D^{pol}$ enzyme, poly(A) and UTP and prevents the picornavirus native VPg from binding to the $3D^{pol}$ enzyme, polyA and UTP.

In another embodiment of the invention, an oligonucleotide constituting adenylate residues (AMP) is administered to a subject in order to inhibit picornavirus replication. The oligonucleotide competes with the poly(A) tail of the picornavirus in complexing with the VPg, UTP and $3D^{pol}$. Since the poly(A) tail of the picornavirus has to compete with the polyA oligonucleotide, replication of the virus is inhibited. Picornaviruses generally have polyA tails of about 70 adenylate residues. The oligonucleotides for use in inhibiting the replication of picornavirus may be anywhere from about five residues to about seventy residues.

In yet another embodiment of the invention, a divalent cation is administered to a subject in order to inhibit picornavirus replication. The divalent cation competitively binds to the metal binding sites on the $3D^{pol}$ enzyme. Certain metals such as magnesium, manganese, zinc and cobalt are known to bind to $3D^{pol}$ and stimulate the uridylylation/ elongation reaction. Other divalent cations, for example, nickel and calcium inhibit the uridylylation/elongation reactions and may therefore be used to compete for the metal binding sites on the $3D^{pol}$ enzyme. One skilled in the art can test different divalent cations for their ability to bind to the $3D^{pol}$ enzyme and inhibit the nucleotidylylation/elongation reactions by substituting a divalent cation for magnesium or manganese in the assays provided in the working examples.

In another aspect of the present invention, ribo and deoxyribo nucleotide analogs of UTP are administered to a subject in order to inhibit picornavirus genome replication. In this embodiment, the ribo and deoxyribo nucleotides competitively bind to VPg, $3D^{pol}$ and the polyA tail of the virus. In one embodiment, 2',3'-Dideoxy-5-fluoruridine triphospate is used as an inhibitor of RNA replication. In another embodiment, 2',3'-Dideoxy-3'fluorouridine triphoshate is used as an inhibitor of RNA replication. In still another embodiment, 2',3'-Dideoxyuridine triphosphate is used as an inhibitor of RNA replication. In yet another embodiment of the present invention, 2',5'-Dideoxyuridine triphosphate is used as an inhibitor of RNA replication.

The present invention also provides in vitro assays useful in screening potential inhibitors of picornaviral RNA replication. The assays provided herein are particularly useful for identifying compositions which inhibit the nucleotidylation of picornaviral VPgs and VPg-dependent elongation.

A first method of identifying an inhibitor of picornaviral replication comprises the steps of incubating for a time and under conditions sufficient to detect uridylylation of picornaviral VPg, a first reaction mixture comprising a buffer with an approximate pH of 7.0–8.0 and a buffer concentration of approximately 10–50 mM; a divalent metal in the form of at least one of approximately 0.1–0.5 mM manganous acetate, approximately 1–7 mM magnesium acetate, approximately 0.1–0.5 mM cobaltous acetate, or approximately 0.1–0.5 mM zinc acetate; approximately 2–10% glycerol; approximately 0.1–1.0 $\mu$g of poly(A); approximately 0.5–2.0 $\mu$g of purified picornaviral RNA polymerase; labeled UTP sufficient to identify labeled uridylylation reaction products; approximately 0.1–100 $\mu$M UTP; and approximately 0.5–5.0 $\mu$g of picornaviral VPg.

A second reaction mixture comprising the same reactants in the same relative amounts as enumerated in the first reaction mixture is incubated with a potential inhibitor of picornaviral replication. The level of uridylylation reaction products obtained in the first and second reaction mixtures are then compared. A decrease in the level of uridylylation reaction products obtained in the second reaction mixture is correlated with the identification of an inhibitor of picornaviral RNA replication.

A second method of identifying an inhibitor of pircornaviral replication comprises the steps of incubating for a time and under conditions sufficient to detect uridylylation of picornaviral VPg, a first reaction mixture comprising a buffer with an approximate pH of 7.0–8.0 and a buffer concentration of approximately 10–50 mM; a divalent metal in the form of at least one of approximately 0.1–0.5 mM manganous acetate, approximately 1–7 mM magnesium acetate, approximately 0.1–0.5 mM cobaltous acetate, or approximately 0.1–0.5 mM zinc acetate; approximately 2–10% glycerol; approximately 0.1–1.0 $\mu$g of purified picornaviral transcript corresponding to an RNA hairpin structure located within the coding sequence of the picornavirus, approximately 0.5–2.0 $\mu$g of purified picornavirus RNA polymerase; approximately 0.2–1.2 $\mu$g of purified picornavirus protein $3CD^{pro}$; labeled UTP in an amount sufficient to detect uridylylated reaction products; 0.1–100 $\mu$M UTP and approximately 0.5–5.0 $\mu$g of synthetic picornavirus VPg.

A second reaction mixture comprising the same reactants in the same relative amounts as enumerated in the first reaction mixture is incubated with a potential inhibitor of picornaviral replication. The level of uridylylation reaction products obtained in the first and second reaction mixtures are then compared. A decrease in the level of uridylylation reaction products obtained in the second reaction mixture is correlated with the identification of an inhibitor of picornaviral RNA replication.

BRIEF DESCRIPTIONS OF THE DRAWINGS

FIG. 1*a* is an autoradiograph showing uridylylation of VPg and VPg-poly(U) synthesis in vitro by poliovirus polymerase $3D^{pol}$ Synthesis of VPgpU(pU) and VPg-poly (U) was a function of VPg concentration. All samples contained [$\alpha$-$^{32}$P]UTP, unlabeled UTP (100 $\mu$M) was added to samples 7–12 and VPg concentration was varied from 0–100 $\mu$M.

Figure 1B:
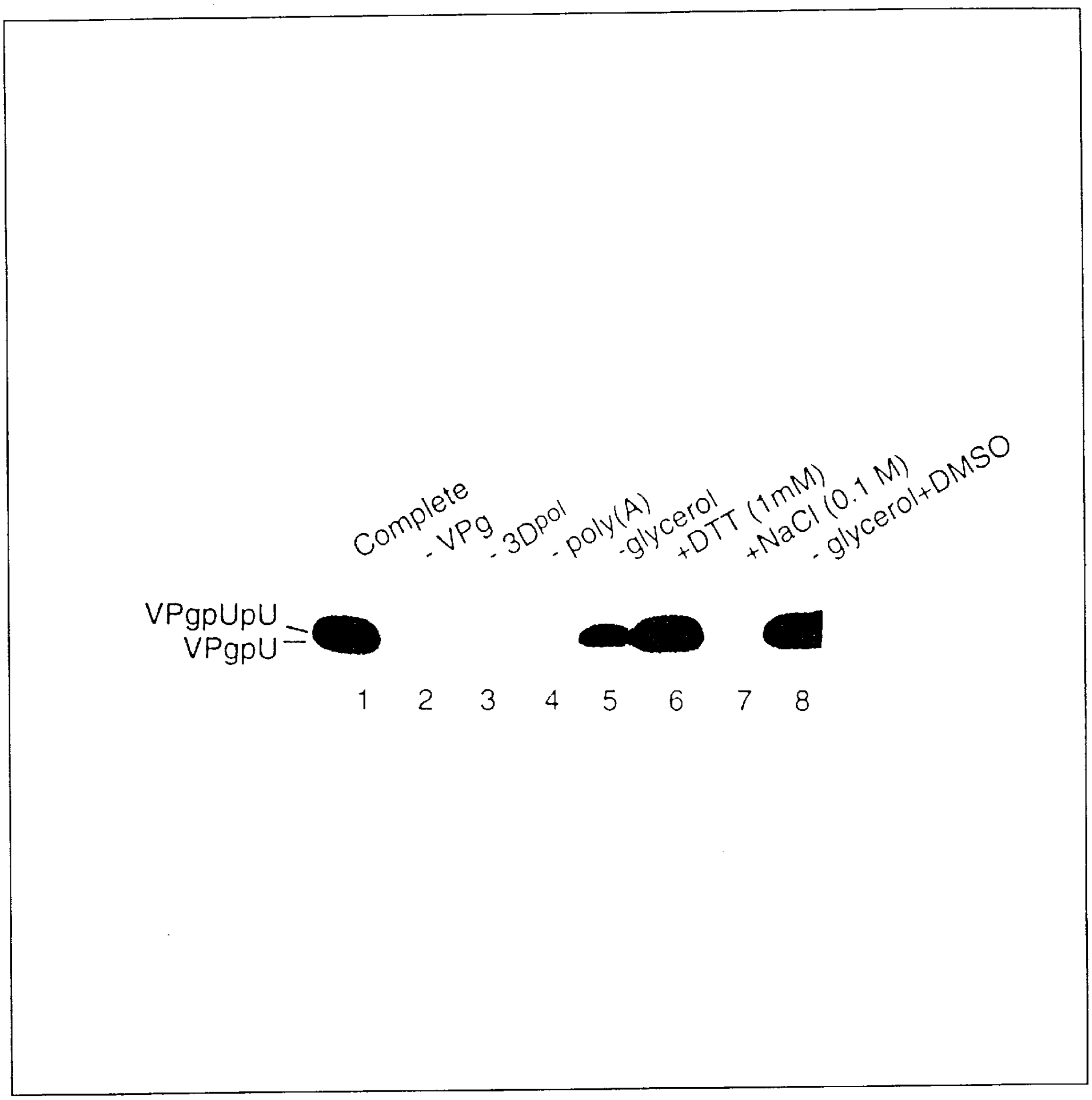

FIG. 1*b* is an autoradiograph showing the requirements for uridylylation of VPg. All samples contained [$\alpha$-$^{32}$P]UTP (0.1 $\mu$M), and various reaction components were omitted or others added.

Figure 2:
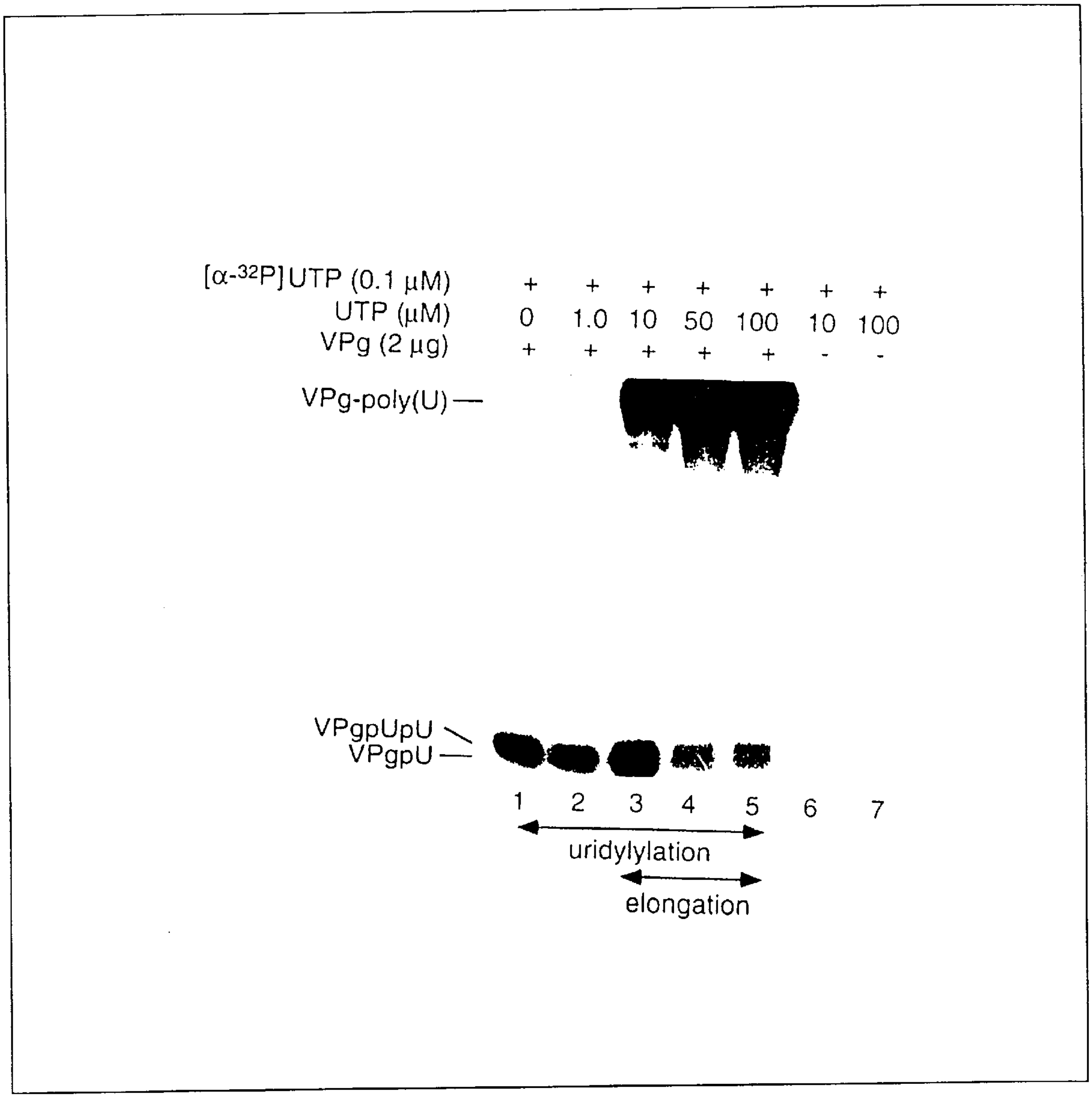

FIG. 2 is an autoradiograph showing uridylylation of VPg and VPg-poly(U) synthesis as a function of UTP concentration. All samples contained [$\alpha$-$^{32}$P]UTp (0.1 $\mu$M) and unlabeled UTP, as indicated. VPg concentration was 50 $\mu$M except the samples shown in lanes 6 and 7 which contained no VPg. It is estimated that in a typical elongation reaction (10 $\mu$M) UTP), 1% of the total label is incorporated into each of VPgpU and poly(U) and 0.4% into VPgpUpU. Of the total VPg added, 0.2% was converted to VPgpU, 0.04% to VPgpUpU, and 0.001% to VPg-poly(U).

Figure 3:
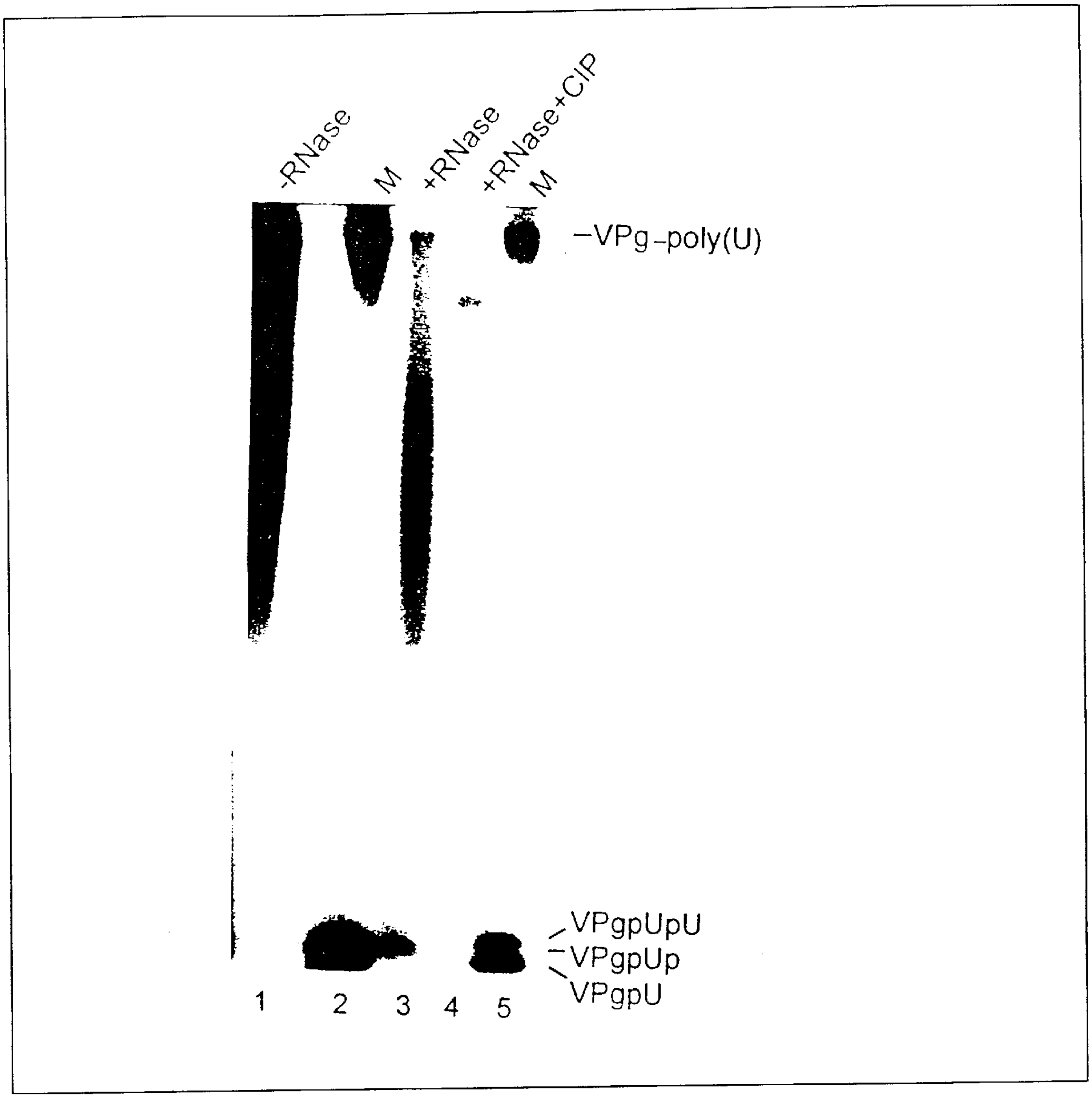

FIG. 3 is an autoradiograph showing the identification of the elongated products as VPg-poly(U). A 240 $\mu$l reaction (10 $\mu$M UTP, 70 $\mu$C [$\alpha$-$^{32}$P]UTP), with carrier DNA added, was extracted with phenol/chloroform and was ethanol precipitated. One third of the isolated polymeric product was untreated (lane 1); one third of the product was treated with RNase A/V1 (lane 3); one third of the product was treated with RNase A/V1 and CIP (lane 4). Aliquots of untreated reaction mixture (lanes 2, 5) are markers (M).

Figure 4A:
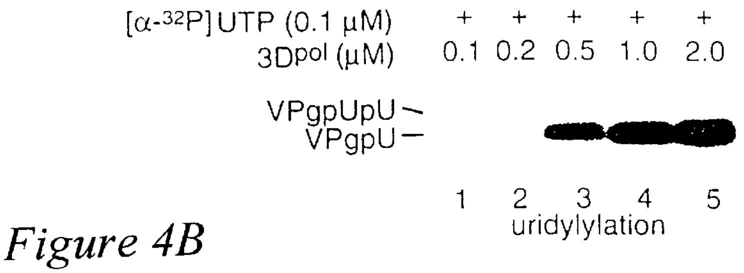

FIG. 4*a* is an autoradiograph showing uridylylation of VPg as a function of $3D^{pol}$ concentration. [$\alpha$-$^{32}$P]UTP was 0.1 $\mu$M, $3D^{pol}$ concentration was varied.

Figure 4B:
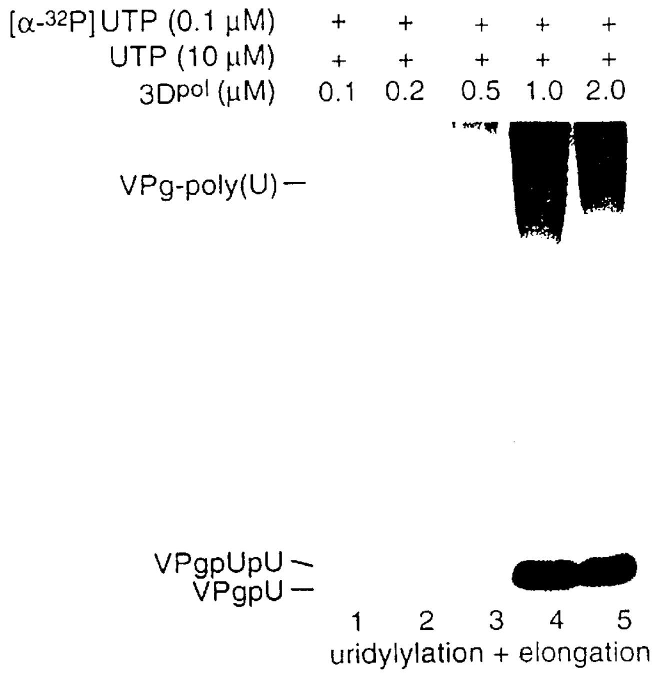

FIG. 4*b* is an autroradiograph showing VPg-poly(U) synthesis as a function of $3D^{pol}$ concentration. 10 $\mu$M UTP was added, $3D^{pol}$ concentration was varied.

Figure 4C:
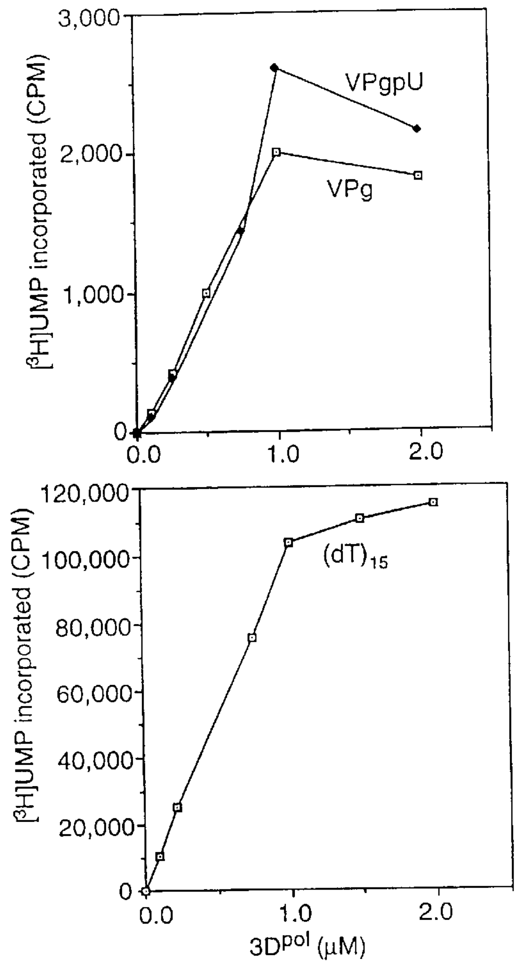

FIG. 4*c* graphically depicts VPg-poly(U) synthesis with VPg, VPgpU or oligo $(dT)_{15}$ primers. [5, 6-$^{3}$H]UTP (1 $\mu$C), 50 $\mu$M UTP were added, the primer was VPg(2 $\mu$g/50 $\mu$M), or VPgpU (2 $\mu$g/43 $\mu$M) or oligo $(dT)_{15}$ (0.5 $\mu$g/0.5 $\mu$M). The amount of [$^{3}$H]UMP incorporated into polymer was determined by a DEAE filter assay. (Paul, A. V., et al. (1994).

Background values in reactions with no $3D^{pol}$ or no VPg added were <90 CPM. It is estimated that the molar ratio of UMP incorporated per primer is roughly 30 for oligo$(dT)_{15}$ and 0.006 for either synthetic VPg or VPgpU.

Figure 5A:
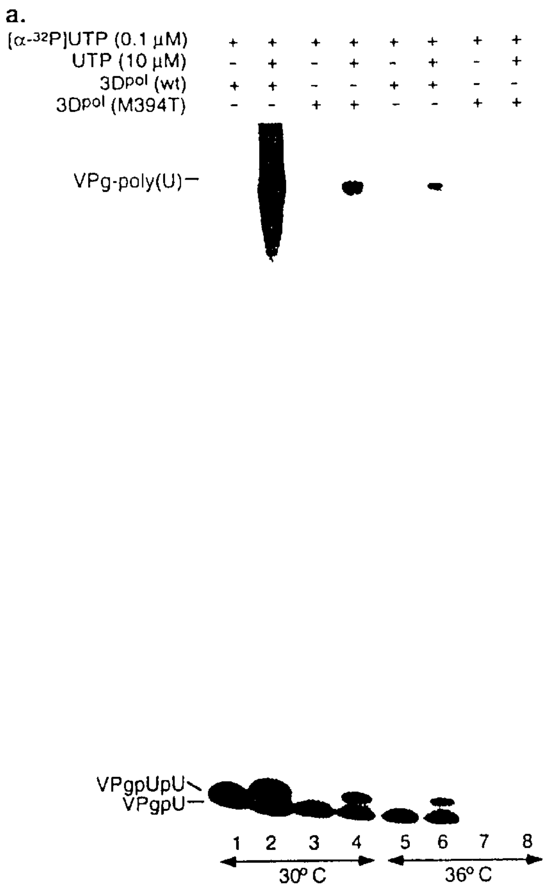

FIG. 5*a* is an autoradiograph showing uridylylation of VPg and VPg-poly(U) synthesis by wt and mutant M394T-$3D^{pol}$ at 30° C. and 36° C. The Standard assay was used with 1 μM wt or mutant M394T-$3D^{pol}$ except that the mixtures were incubated at either 30° C. or 36° C. Samples 2, 4, 6 and 8 contained 10 μM UTP.

Figure 5B:
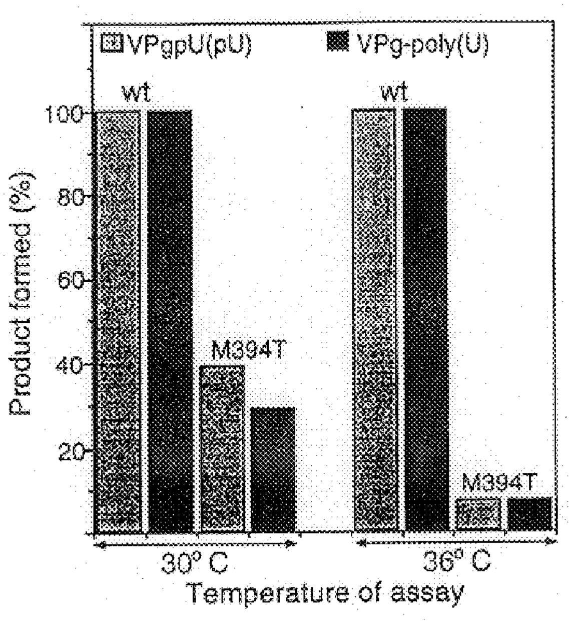

FIG. 5*b* graphically depicts the quantitation of product made by wt and mutant M394T-$3D^{pol}$. The yield of VPgpU (pU) was determined by phosphorimager analysis from FIG. 5*a*, lanes 1, 3, 5 and 7, the yield of VPg-poly(U) from lanes 2, 4, 6 and 8. The amount of product [VPgpU(pU) or VPg-poly(U)], made at either temperature by the wt enzyme, was taken as 100%.

Figures 6A, 6B, 6C:
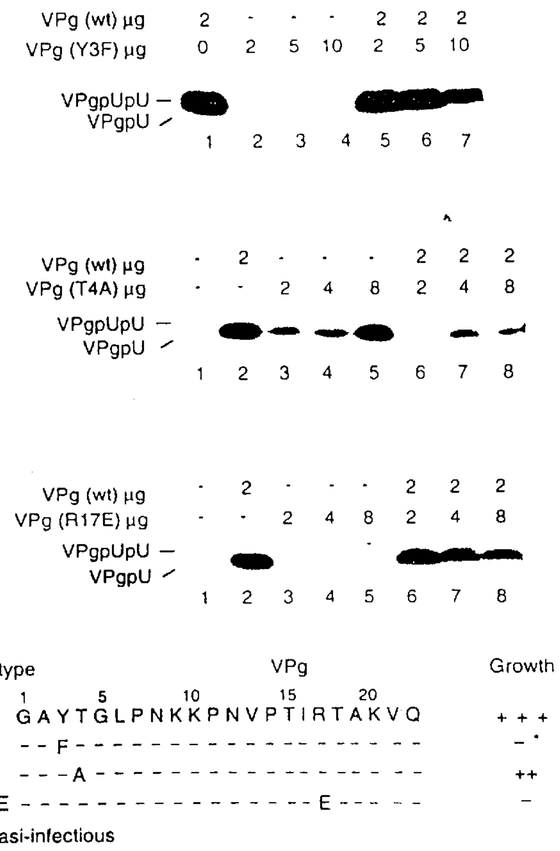

FIG. 6*a* is an autoradiograph showing Wild-type and mutant VPg peptides as substrates for uridylylation by $3D^{pol}$, specifically comparing wt VPg and Y3F peptides. Reaction mixtures contained wt or mutant VPg peptides.

FIG. 6*b* is an autoradiograph comparing wt VPg and T4A peptides in the reaction described in FIG. 6*a*.

FIG. 6*c* is an autoradiograph comparing wt VPg and R17E peptides in the reaction described for FIG. 6*a*. The amino acid sequence of wt, Y3F, T4A and R17E peptides is shown along with the viability of engineered genomes containing the wt or mutant VPg peptides (SEQ ID NOS:44–47). Cao, X., et al. (1995); Kuhn, R. J. et al. (1988); Xiang, W., et al. (1995). The asterisk indicates "quasi infectious" virus. Cao, X., et al. (1995).

Figure 6D:
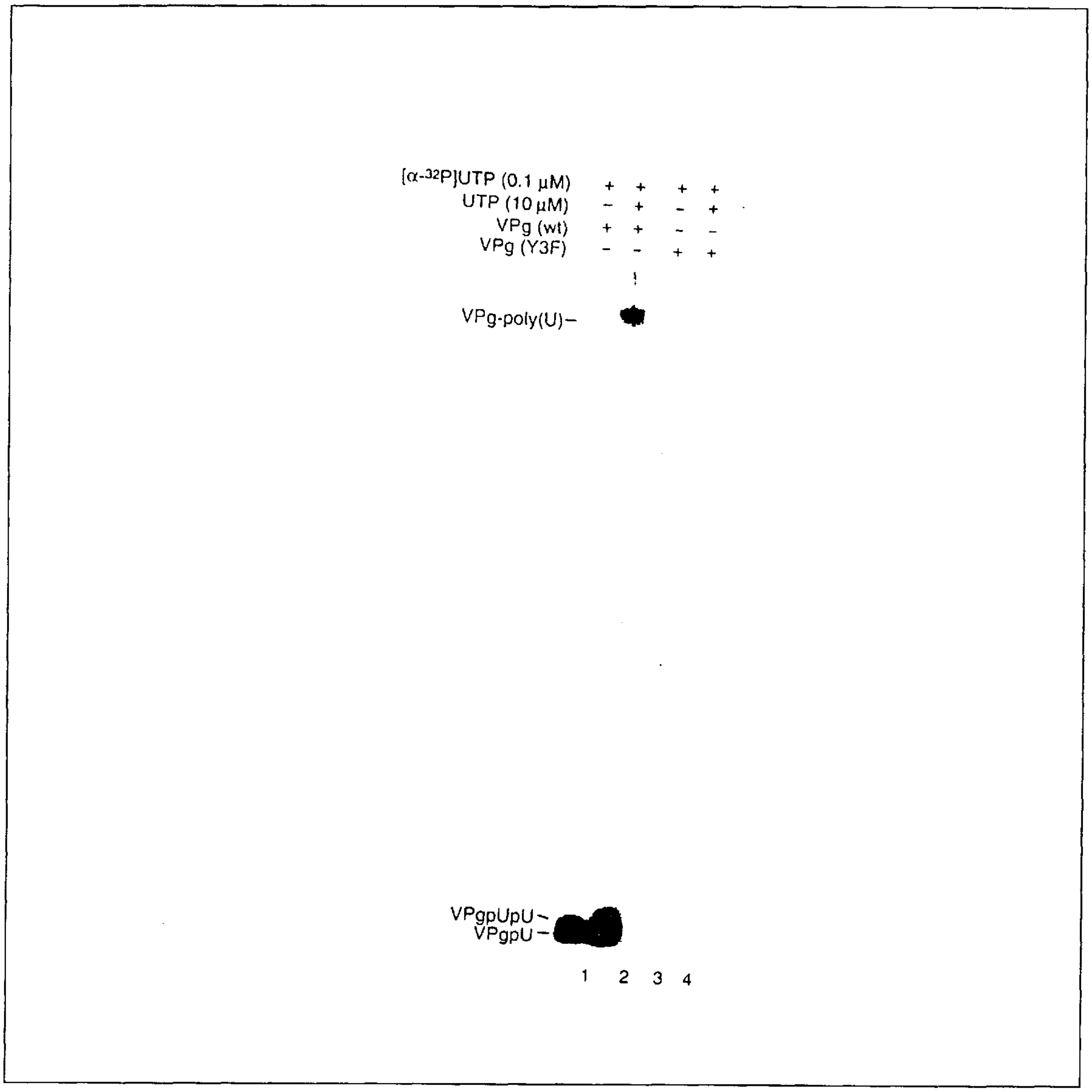

FIG. 6*d* is an autoradiograph comparing wt VPg and (Y3F) peptides as substrates for uridylylation coupled to elongation.

FIG. 7 illustrates the initiation of poliovirus RNA replication discovered in accordance with the present invention (SEQ ID NO:48). Poliovirus polymerase $3D^{pol}$ complexed with the terminal protein VPg binds at or near the 3'-terminal end of the poly(A) tail. The complementary nucleotide UTP is selected and positioned near the tyrosine residue of VPg. UTP is bound to the complex by its attraction to the positively charged R17 residue of VPg. The polymerase catalyzes the formation of a phosphodiester bond between UMP and the hydroxyl group of tyrosine. The 3'hydroxyl group of peptidyl-nucleotide then serves to prime polynucleotide synthesis.

Figure 8:
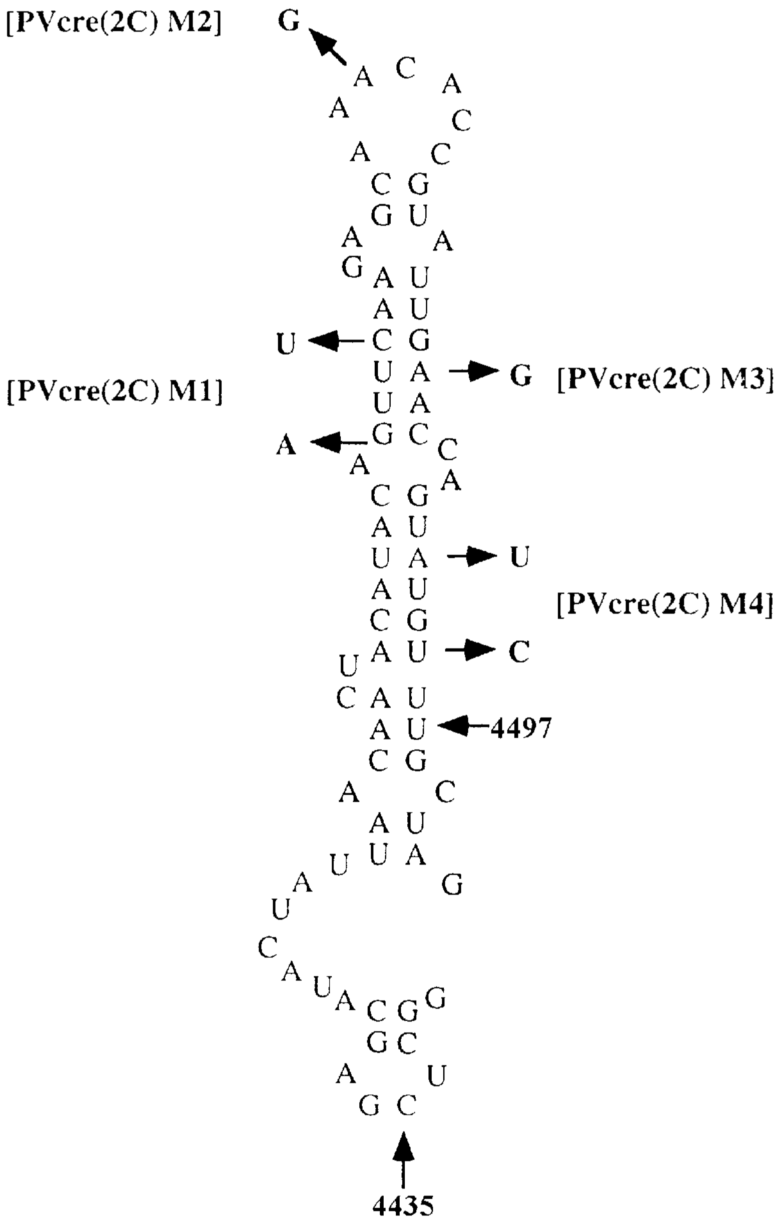

FIG. 8 illustrates the predicted structure (SEQ ID NO:49) of the RNA hairpin designated PVcre(2C) that is located in the 2C coding region (nucleotides 4435–4502) of the poliovirus RNA. Mutations which were introduced into the wt sequences are indicated in bold letters.

Figure 9:
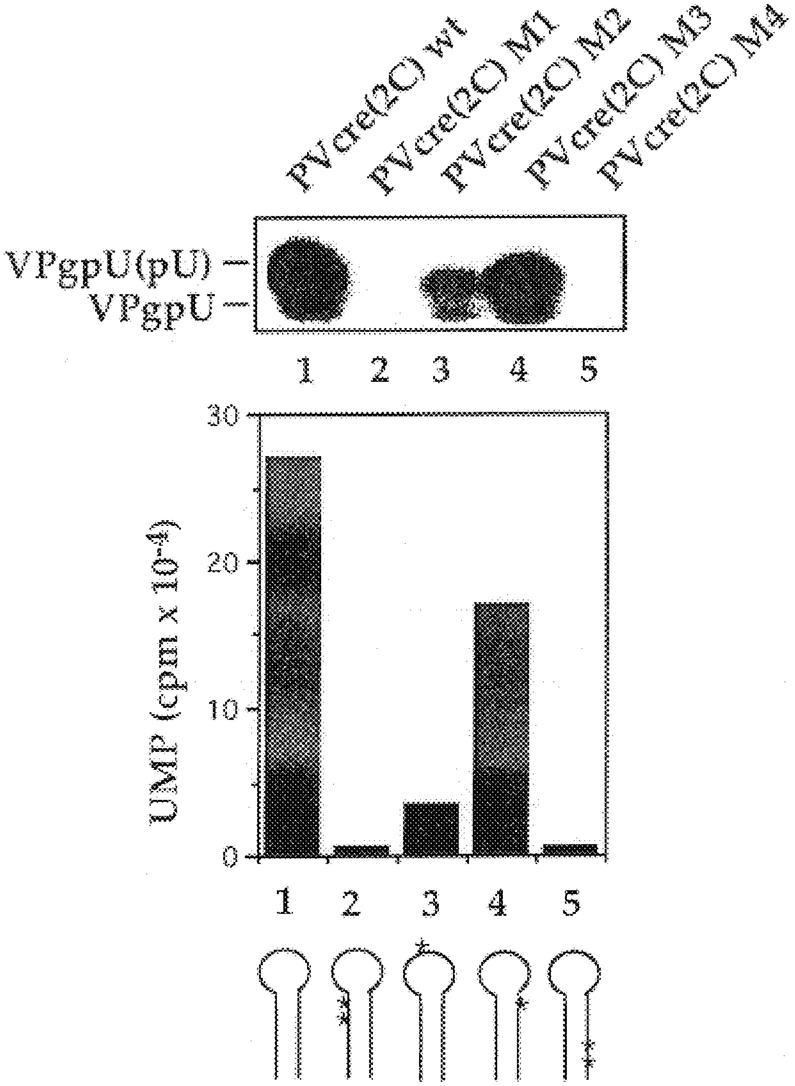

FIG. 9 provides an autoradiograph and phophorimager quantification of the uridylylation of VPg by $3D^{pol}$ on wt and mutant cre(2C) templates. All samples contained $3CD^{pro}$ and 3.5 mM $Mg^{++}$ (assay 2). The location of the mutations in the cre(2C) template are indicated in FIG. 8.

Figure 10:
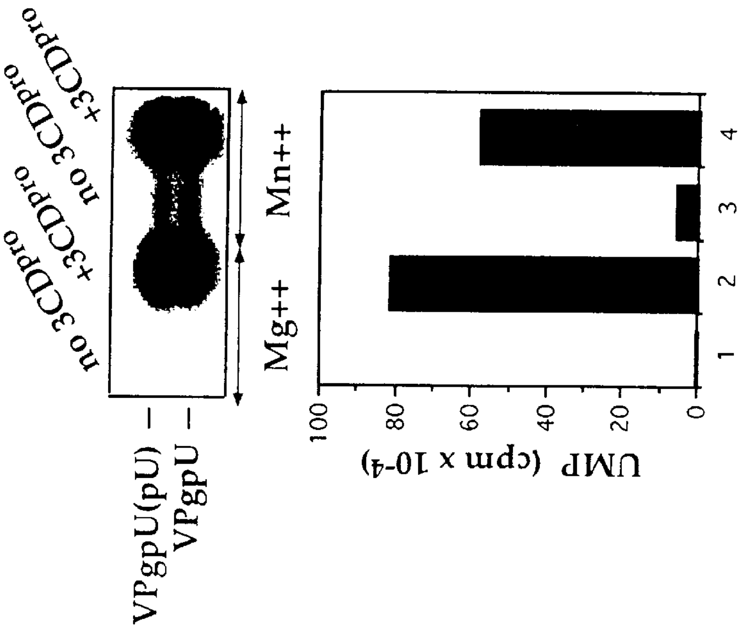

FIG. 10 provides an autoradiograph and phosphorimager quantification of the uridylylation of VPg by $3D^{pol}$ on the cre(2C) template in the presence or absence of $3CD^{pro}$. All samples contained the cre(2C) RNA as template. Either Mg++ or Mn++ was used in assay 2.

DETAILED DESCRIPTION OF THE INVENTION

In accordance with the present invention, it has been surprisingly found that VPg is uridylylated by the virus-encoded RNA polymerase $3D^{pol}$, the reaction requiring only VPg, $3D^{pol}$, poly(A), UTP and magnesium ions (uridylylation). The product, VPgpU(pU) subsequently serves as a primer for $3D^{pol}$ in virus-specific RNA synthesis (elongation). Uridylylation is highly specific; no other nucleoside triphospate or homopolymer can substitute UTP and poly(A).

Uridylylation is greatly stimulated if manganese ions are present instead of magnesium ions. This sequence of reaction involving protein-primed RNA synthesis, is unprecedented and has not been described before. The VPgs of all picornaviruses are between 20 and 26 amino acids long; uridylylation occurs in all cases at the third residue from the N-terminus, a tyrosine. All picornaviruses carry a poly(A) tail at the 3' end, the site where genome replication commences. Since genome replication of picornaviruses depends upon the linkage of VPg to the viral genome, this reaction serves to initiate RNA synthesis of all picornaviruses and is an unusually attractive target for the development of anti-picornaviral drugs.

The present invention therefore provides methods for inhibiting picornavirus genome replication. Presently, there are no commercially available antiviral drugs effective against picornaviruses despite the fact that such viruses cause a vast incidence of human disease. The common cold alone causes tens of millions of work hours lost in the United States during one year. Some of the diseases caused by picornaviruses are life threatening, e.g., heart disease, meningitis, and hepatitis. Other diseases caused by picornaviruses are benign, e.g., the common cold caused by rhinovirus. Because protein priming of RNA does not naturally occur in the cells of primates, inhibition of picornavirus genome replication by interference with VPg-nucleotidylylation and elongation in order to prevent or ameliorate diseases caused by picornaviruses will not adversely effect body cells. Rapid emergence of resistance is unlikely due to the bi-modal nature of the reaction.

In accordance with the present invention inhibitors of picornavirus replication are administered in a therapeutically effective amount to a subject in order to treat those diseases caused by picornaviruses. Examples of inhibitors include VPg, VPg analog, VPg homolog or biologically active fragment thereof. Other examples of inhibitors include oligonucleotides consisting essentially of adenylate (AMP) residues. Still other inhibitors of picornavirus replication include divalent cations such as calcium and nickel. Yet other inhibitors of picornavirus include ribo or deoxyribo nucleotides. Any composition which serves to inhibit the nucleotidylylation/elongation reactions of picornavirus is contemplated for use in the methods of the present invention.

The inhibitors of RNA replication for use in the methods of the present invention may be administered to a human patient preferably as a pharmaceutical composition in a therapeutically effective amount. The pharmaceutical compositions of the present invention contain a therapeutically effective dose of an inhibitor of picornavirus replication, e.g. the VPg protein, homologs or analogs thereof or else contain a biologically active fragment of the VPg protein, homologs or analogs thereof together with a pharmaceutically acceptable carrier. The term "therapeutically effective amount" means the dose needed to effectively inhibit picornavirus genome replication. For purposes of the present invention, the terms "treat" or "treatment" include preventing, inhibiting, reducing the occurrence of and/or ameliorating the replication of picornaviruses.

As used herein, "analogs" is meant to include substitutions or alterations in the amino acid sequence of any VPg protein, which substitutions or alterations (e.g., additions and deletions) maintain the protein's ability to complex with $3D^{pol}$, poly(A) and UTP, which complexing facilitates transfer of UMP to the hydroxyl of Y3 in VPg. Table 1 lists the amino acid sequences of VPg proteins from different Enterovirus and Rhinovirus species contemplated for use in the methods of the present invention.

The methods may also be extended to other picornaviruses causing disease in humans (e.g., hepatitis A virus) or animals (e.g., foot-and-mouth disease virus, swine vesicular disease virus). The VPgs of all of these viruses carry the Y residue at position three (Table 1). "PV1M" designates the Mahoney strain of poliovirus used in the working examples of the present invention. For purposes of the present invention, the term "analog" includes amino acid insertional derivatives of the VPg proteins listed in Table 1 such as amino and/or carboxyl terminal fusions as well as intrasequence insertions of single or multiple amino acids. Insertional amino acid sequence variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue in the sequence has been removed and a different residue inserted in its place. Where the protein is derivatized by amino acid substitution, amino acids are generally replaced by other amino acids having similar physical chemical properties such as hydrophobicity, hydrophilicity, electronegativity, bulky side chains and the like.

Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between glycine and serine. Additionally, the substitution of a basic residue such as lysine, arginine or histidine for another or the substitution of an acidic residue such as aspartic acid or glutamic acid for another is also contemplated.

As used herein, the term "analogs" also encompasses homologs of poliovirus VPg, i.e., corresponding amino acid sequences derived from other VPg proteins, e.g., those listed in Table 1. As used herein, the term "biologically active fragments" refer to fragments of VPg or VPg analogs and homologs which do not encompass the entire length of a VPg peptide but which nevertheless maintain the ability to complex with $3D^{pol}$, poly(A) and UTP, which complex facilitates transfer of UMP to the hydroxyl Y3 of VPg.

VPg amino acid variants may be readily made using peptide synthetic techniques well known in the art such as solid phase peptide synthesis (Merrifield synthesis) and the like or by recombinant DNA techniques well known in the art. Techniques for making substitution mutations at predetermined sites in DNA include for example M13 mutagenesis. Manipulation of DNA sequences to produce substitutional, insertional, or deletional variants are conveniently described elsewhere such as Sambrook et al., 1989 Molecular Cloning: A Laboratory Manual, Cold Spring Harbor Laboratories, Cold Spring Harbor, N.Y.

For purposes of the present invention, analogs of VPg also include single or multiple substitutions, deletions and/or additions of any component(s) naturally or artificially associated with the VPg such as carbohydrate, lipid and/or other proteinaceous moieties. All such molecules are encompassed by the term VPg analogs.

The formulation of pharmaceutical compositions is generally known in the art and reference can conveniently be made to Remington's Pharmaceutical Sciences, 17th ed., Mack Publishing Co., Easton, Pa. Formulation of the inhibitors of picornavirus genome replication for use in the present invention must be stable under the conditions of manufacture and storage and must also be preserved against the contaminating action of microorganisms such as bacteria and fungi. Prevention against microorganism contamination can be achieved through the addition of various antibacterial and antifungal agents.

The pharmaceutical forms of inhibitors of picornavirus replication suitable for infusion include sterile aqueous solutions or dispersions and sterile powders for the extemporaneous preparation of sterile injectable solutions or dispersion. In all cases, the form must be sterile and must be fluid to the extent that easy syringability exists. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants, or vegetable oils. Sterilization can be accomplished by any art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject inhibitors of picornavirus genome replication is accomplished by incorporating the compositions in the required amount in the appropriate solvent with various ingredients enumerated above, as required, followed by sterilization, preferably filter sterilization. To obtain a sterile powder, the above solutions are vacuum-dried or freeze-dried as necessary.

The subject inhibitors of picornavirus genome replication are thus compounded for convenient and effective administration in pharmaceutically effective amounts with a suitable pharmaceutically acceptable carrier in a therapeutically effective dose.

As used herein, the term "pharmaceutically acceptable carrier and/or diluent" includes any and all solvents, dispersion media, antibacterial and antifungal agents, microcapsules, liposomes, cationic lipid carriers, isotonic and absorption delaying agents and the like which are not incompatible with the active ingredients, e.g. VPg, VPg analogs, homologs or biologically active fragment thereof, oligonucleotide consisting of AMP residues, divalent cations, ribo or deoxyribo nucleotide. The use of such media and agents for pharmaceutical active substances is well known in the art. Supplementary active ingredients may also be incorporated into the compositions and used in the methods of the present invention.

The precise therapeutically effective amount of picornavirus genome replication inhibitor to be used in the methods of this invention applied to humans can be determined by the ordinarily skilled artisan with consideration of individual differences in age, weight, extent of picornavirus infection and condition of the patient.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly depend on the unique characteristics of the active material (e.g. VPg protein, VPg analogs, or fragments thereof, divalent cations, oligonucleotides consisting of AMP residues), and the limitations inherent in the art of compounding such an active material for inhibition of picornavirus genome replication as herein disclosed in detail.

The principal active ingredient is compounded for convenient and effective administration in effective amounts with a suitable pharmaceutically acceptable carrier in dosage unit form as hereinabove disclosed. In the case of compositions containing supplementary active ingredients, the dosages are determined by reference to the usual dose and manner of administration of the ingredients.

Packaging material used to contain the picornavirus replication inhibitor active ingredient can comprise glass, plastic, metal or any other suitable inert material so long as the packaging material does not chemically react with any of the ingredients contained therein.

The picornavirus genome replication inhibitor may be administered in a manner compatible with the dosage formulation and in such amount as will be therapeutically effective. The compositions of the invention may be administered in any way which is medically acceptable which may depend on the disease condition. Possible administration routes include injections, by parenteral routes such as intravascular, intravenous, intra-arterial, subcutaneous, intramuscular, intratumor, intraperitoneal, intraventricular, intraepidural or others, as well as oral, nasal, ophthalmic, rectal, topical, or by inhalation. The compositions may also be directly applied to tissue surfaces during surgery. Sustained release administration is also specifically included in the invention, by such means as depot injections or erodible implants. Administration via nasal, ophthalmic and inhalation routes are especially favored for inhibition of rhinovirus replication.

The present invention also provides methods for identifying compositions useful in inhibiting picornaviral RNA replication. In accordance with the present invention, these methods comprise in vitro assays of VPg uridylylation which assays can identify compositions such as elements, molecules, chemical compounds, and reagents that specifically inhibit the uridylylation of picornaviral VPgs and VPg-dependent elongation.

In accordance with the present invention, there are provided two different types of assays. The major difference between the two types of assays described herein is the nature of the template for the uridylylation reaction. In a first assay, poly(A), a homopolymer is used as template. In a second assay, an RNA hairpin structure that is located within the coding region of the picornavirus RNA genome, is used as template. The existence of a hairpin RNA structure in the poliovirus genome was reported by Goodfellow et al., *EUROPIC* 98, Abstract V42, Jena, Germany, Sep. 5–11, 1998.

An assay utilizing the homopolymer poly(A) is preferred for use in initial screening of inhibitors. A second more specific assay utilizing a picornavirus RNA hairpin structure is preferred for use as an additional screen if a promising inhibitor is obtained in the first assay system. In addition, the second assay offers a method to screen for specific antisense oligonucleotide inhibitors.

In a first type of in vitro assay (Assay I), a control reaction mixture contains approximately 10–50 mM buffer at a pH in the range of about 7.0 to about 8.0; a divalent metal such as approximately 0.1 to 0.5 mM manganous acetate or approximately 1–7 mM magnesium acetate or approximately 0.1–0.5 mM cobaltous acetate or approximately 0.1 to 0.5 mM zinc acetate; approximately 2 to 10% glycerol; approximately 0.1 to approximately 1.0 $\mu$g poly(A); approximately 0.5 to 2.0 $\mu$g purified picornavirus RNA polymerase; labeled UTP in an amount sufficient to detect labeled uridylylation reaction products, approximately 0.1 to 100 $\mu$M UTP and approximately 0.5 to 5 $\mu$g of picornavirus VPg.

The mixture is incubated for a time and under conditions sufficient for the uridylylation reaction to be carried out. As defined herein, a sufficient time can be anywhere from about five minutes to several hours or more. In a preferred embodiment, the length of reaction is about one hour.

A preferred buffer for use in the reactions is Hepes (N-2-hydroxyethylpiperazine-N'-2-ethanesulfonic acid). In a preferred embodiment, the reaction volume is between 15–50 $\mu$l. In a more preferred embodiment, the reaction volume is 20 $\mu$l. The temperature at which the reaction mixture is incubated may be in the range of from about 30° C. to about 37° C. In a preferred embodiment, the incubation temperature is approximately 33° C.

UTP may be labeled with a number of different reporter molecules. As used herein, a "reporter molecule" is a molecule which provides an analytically identifiable signal allowing detection when attached to UTP and when incorporated into uridylylation or elongation reaction products. Reporter molecules which can provide analytically identifiable signals include, e.g., fluorophores, chemiluminescent molecules, bioluminescent molecules, radioisotopes and the like. Reporter molecules can also be detected by addition of another reagent, e.g., by adding a substrate for an enzyme reporter molecule, by binding an antibody conjugated to an enzyme or other reporter molecule, and the like. For example, a biotin 16 reporter molecule attached to UTP can be detected by binding an anti-biotin fluorescent antibody. UTP labeled with such reporter molecules may be obtained through commercial sources. For example, radiolabeled UTP may be obtained by Amersham or Dupont NEN. Biotin 16 labeled UTP may be obtained from Roche.

In a preferred embodiment, UTP is labeled with a radioisotope such as $^{3}H$, $^{33}P$, or $^{32}P$. [$^{\alpha\text{-}32}P$] may be purchased from DuPont NEN or Amersham. [5,6-$^{3}$H]UTP may be obtained from ICN. In a preferred embodiment, [$^{32}$P]-UTP is used. The amount of [$^{32}$P]-UTP used in the reactions of the present invention is preferably in the range of approximately 0.5 $\mu$C to 10.0 $\mu$C.

The in vitro assays of the present invention may be tailored for use with VPgs and RNA polymerases from different picornaviruses in order to identify a composition which inhibits replication of a particular picornavirus. Thus, a particular species of picornavirus RNA polymerase may be isolated using methods known in the art. The corresponding VPg from the same picornavirus may be synthesized using well known chemical methods for use in the in vitro reactions. Table 1 lists a number of picornaviruses VPgs which may be used in the reactions of the present invention. cDNAs made from different picornaviruses are available from the American Type Culture Collection (ATTC), 10801 University Boulevard, Manassas, Va., 20110-2209. The picornavirus cDNAs may be used in subcloning the RNA polymerase coding sequences for production of RNA polymerase. Poliovirus (Mahoney) cDNA is available from the ATCC as Accession No. 45149. VPgs may also be chemically synthesized using well known methods.

For example, the uridylation/elongation reactions may be assayed using poliovirus RNA polymerase and VPgs from poliovirus and Rhinovirus.

The experimental reaction mixture of Assay I comprises the same reactants in the same relative amounts and under the same conditions as the control reaction mixture and additionally comprises a composition to be screened as a potential inhibitor of picornaviral RNA replication. Such composition may include for example, an element, molecule, chemical compound, or reagent. The amount of a particular composition to be tested as a potential inhibitor in the reactions of the present invention is empirical. One skilled in the art is familiar with methods of adjusting concentrations of different compositions in order to best identify the effects of the composition in the experimental reaction.

The reaction products from both the control and experimental reactions, i.e., labeled uridylylated VPg in the form of VPgpU and VPgpU(pU) are analyzed by any number of well known methods for analysis of labeled products. For example, reaction products may be qualitatively analyzed by SDS/polyacrylamide gel electrophoresis (PAGE) followed by autoradiography. Quantification of the labeled reaction products can be achieved using a phosphorimager. In a preferred embodiment, an approximately 12–15% acrylamide-Tris/Tricine/SDS gel is used to analyze reaction products. In a more preferred embodiment, a 13.5% acrylamide-Tris/Tricine/SDS gel (BioRad) is used to analyze reaction products.

By comparing the levels of labeled uridylylation products between the experimental and control reactions, one skilled in the art is able to correlate a qualitative decrease in the level of uridylylation products in the experimental reaction with the identification of an inhibitor of picornaviral RNA replication. Methods for analyzing labeled reaction products also include well known quantification methods such as for example, paper or column chromatography followed by phosphorimaging or scintillation counting, respectively.

In a second type of in vitro assay (Assay II), a control reaction mixture contains approximately 10 to 50 mM buffer at an approximate pH of 7.0 to 8.0; a divalent metal such as approximately 0.1 to 0.5 mM manganous acetate or approximately 1–7 mM magnesium acetate, or 0.1 to 0.5 mM cobaltous acetate, or 0.1 to 0.5 mM zinc acetate; approximately 2 to 10% glycerol, approximately 0.1 to 1.0 $\mu$g purified picornavirus RNA transcript having a hairpin structure within the coding region, approximately 0.5 to 2.0 $\mu$g purified picornavirus RNA polymerase, approximately 0.2 to 1.2 $\mu$g of purified picornavirus protein $3CD^{pro}$, labeled UTP in an amount sufficient to detect uridylylation reaction products, approximately 0.1 to 100 $\mu$M UTP and approximatley 0.5 to 5.0 $\mu$g of picornavirus VPg.

The mixture is incubated for a time and under conditions sufficient for the uridylylation reaction to be carried out. As defined herein, a sufficient time can be anywhere from about five minutes to several hours or more. In a preferred embodiment, the length of reaction is about one hour.

Preferably, the reaction volume is between 15–50 ul. In a more preferred embodiment, the reaction volume is 20 $\mu$l. Preferably, magnesium acetate is used in the reaction. The mixture is incubated for a sufficient time for the uridylylation reaction to be carried out in the control reaction. In a preferred embodiment, the length of reaction is about one hour. The purified picornavirus RNA transcript having a hairpin structure within the coding region preferably comprises a loopo which contains an AMP rich sequence. In a preferred embodiment, the AMP rich sequence comprises the nucleotides AAACA. In the case of poliovirus, the plus strand sequence of the poliovirus hairpin structure has nucleotides 4435 to 4502 as depicted in FIG. 8 (SEQ ID NO:1). In the case of Rhinovirus 14, the plus strand sequence of a hairpin structure (nucleotides 2318–2413) has the sequence set forth in SEQ ID NO:2.

The temperature at which the reaction mixture is incubated may be in the range of from about 30–37° C. In a preferred embodiment, the incubation temperature is 33° C. As described for use in the first type of assay (Assay I), UTP may be labeled with any number of different reporter molecules. As described above, in a preferred embodiment, UTP is labeled with a radioisotope such as $^{3}H$, $^{33}P$, or $^{32}P$. In a preferred embodiment, [$^{32}$P]-UTP is used in the assays of the present invention. The amount of [$^{32}$P]-UTP used in the reactions of the present invention is preferably in the range of approximately 0.5 $\mu$C to 10.0 $\mu$C.

The experimental reaction mixture of Assay II comprises the same reactants in the same amounts and under the same conditions as the control reaction mixture and additionally comprises an element, molecule, chemical compound, or reagent to be screened as a potential inhibitor of picornaviral RNA replication. As described above, the reaction products from both the control and experimental reactions are analyzed by any number of methods for analysis of labeled products. For example, as described above, the reaction products from both the control and experimental reactions may be analyzed by SDS/PAGE followed by autoradiography. In a preferred embodiment, an approximately 12–15% acrylamide-Tris/Tricine/SDS gel is used to analyze reaction products. In a more preferred embodiment, a 13.5% acrylamide-Tris/Tricine/SDS gel is used to analyze reaction products.

$3CD^{pro}$ is a precursor to picornavirus RNA polymerase. Thus picornaviral cDNAs available through the ATCC or other depository may be used to subclone the $3CD^{pro}$ coding sequence for production of $3CD^{pro}$ for use in Assay II.

By comparing the level of uridylylation products between the experimental and control reactions, one skilled in the art is able to correlate a qualitative decrease in the level of uridylylation products in the experimental reaction with the identification of an inhibitor of picornaviral RNA replication. The quantification methods described for use in Assay I are also applicable for use in Assay II.

Examples of inhibitors which may be screened in the assays of the present invention include antisense oligonucleotides. Such oligonucleotides may be designed to hybridize to a hairpin structure within the coding region of a picornavirus RNA. Although picornaviruses possess hairpin structures in the 5' and 3' untranslated sequences, a hairpin structure located within the coding sequence is intimately associated with the initiation of picornavirus replication. Specifically, the uridylylation of VPg occurs on an AMP rich sequence within the coding sequence hairpin loop. Thus, by locating the hairpin loop within a picornavirus RNA and identifying the nucleotide sequence of the loop, complementary sequences which hybridize to the entire loop or portions of the loop can be designed. For example, antisense oligonucleotides which hybridize to cre(2C) RNA sequences in poliovirus RNA may be designed and tested for the ability to prevent uridylylation of VPg on the RNA template. In this aspect of the invention, the second type of above-described assay is used. For example, an oligonucleotide which hybridizes to SEQ ID NO:1 is particularly contemplated for testing as an inhibitor. Oligonucleotides in the range of from about 8 to about 70 nucleotides long may be used to test for inhibition of picornaviral replication. Preferably, an oligonucleotide is from about 10 to about 25 nucleotides in length.

Nucleotide analogues may also be tested for inhibition of uridylylation using the assays of the present invention. Ribonucleotides or deoxyribonucleotides may be used. In accordance with the present invention, a nucleotide analogue which is a potential inhibitor should compete with UTP only in the nucleotidylylation reaction but not with the utilization of UTP during cellular RNA synthesis. In this aspect of the invention, the above-described first type of assay is used.

VPg analogs as defined supra are also potential candidates as inhibitors of picornaviral RNA replication. Such peptides compete with the wild type peptide in the uridylylation reaction. The above-described first assay is preferably used in this aspect of the invention. Thus, the RNA polymerase and a first VPg (i.e. wt) in the reaction are from the same picornavirus and a second VPg (i.e., a VPg analog) which competes with the wt VPg is used to test for its effectiveness in inhibiting the replication of picornavirus.

Metal ions may also be tested as potential inhibitors of uridylylation in the above-described in vitro assays. An ideal metal inhibitor competes with magnesium ions in the uridylylation of VPg by $3D^{pol}$. The above-described first assay is also preferably used in this aspect of the invention.

In addition, randomly synthesized chemicals such as those selected from libraries of chemicals, may be used to screen for inhibition of uridylylation and elongation.

The invention is further illustrated by the following specific examples which are not intended in any way to limit the scope of the invention.

EXAMPLE 1

Methods

Assay of Uridylylation and of VPg-poly(U) Synthesis

Poliovirus polymerase was expressed in *E. coli* from plasmid pT5T-3D, supplied by K. Kirkegaard, Stanford University and purified as described by Pata, J. D., et al. (1995) *RNA* 1:466–477. The enzyme was >99% pure as judged by Coomassie gel staining. Purified mutant M394T-$3D^{pol}$ was supplied by J. Lyle and K. Kirkegaard, Stanford University. The chemical synthesis of VPg peptides and of VPgpU was as described in Dreef-Tromp, C. M., et al. (1992) *Nucleic Acids Research* 20, 2435–2439. [$\alpha$-$^{32}$P]UTP was purchased either from DuPont NEN (3000 c/mmol) or Amersham (800 C/mmol), [5,6-$^{3}$H]UTP (43C/mmol) was a product of ICN. RNase V1 was product of Pharmacia, RNase A and CIP (alkaline phosphatase, calf intestine) were purchased from Boehringer Mannheim). Poly(A) was purchased from Pharmacia.

Uridylylation of VPg was assayed in a reaction mixture (20 $\mu$l) that contained 50 mM Hepes buffer pH 7.0–7.5, 3.5 mM magnesium acetate, 6–8% glycerol, 0.5 $\mu$g/0.35 $\mu$M poly(A) (about 200 nt long), 2 $\mu$g/50 $\mu$M synthetic VPg, 1 $\mu$g/1 $\mu$M purified $3D^{pol}$, 2 $\mu$C/0.1 $\mu$M[$\alpha$-$^{32}$P]UTP. To measure VPg-poly(U) synthesis, unlabeled UTP (>10 $\mu$M), was also included in the reaction mixture. Samples were incubated at 33° C. for 60 min and analyzed by tricine-sodium dodecyl sulfate-polyacrylamide gel electrophoresis (BioRad) with 13.5% polyacrylamide concentration. Gels were dried without fixing and subjected to autoradiography. Incorporation of $^{32}$P into reaction products was quantitated using a phosphorimager (Molecular Dynamics Storm 860).

EXAMPLE 2

Synthetic VPg was incubated with purified $3D^{pol}$, the primer-dependant RNA transcriptase (Flanegan, J. B., et al. (1977) *Proc. Natl. Acad. Sci. USA* 74, 3677–3680.), and [$\alpha$-$^{32}$P]UTP. No products were formed unless poly(a) was added to the reaction mixture. $3D^{pol}$ then synthesized two products with characteristics of VPgpU and VPgpU(pU) (Takegami, T., et al. (1983); Takeda, N., et al. (1986); Toyoda, H., et al. (1987)), referred to in the following as VPgpU(pU) (FIG. 1*a*, lanes 1–6; FIG. 1*b*). Digestion of $^{32}P$-labeled VPgpU(pU) with HCl and analysis of the products by thin-layer chromatography or paper electrophoresis showed that the tyrosine residue was uridylylated. Glycerol (6%) or dimethyl sulfoxide (5%) were, surprisingly, strong stimulants for uridylylation (FIG. 1*b*, lanes 5 and 8, respectively), whereas 100 mM NaCl inhibited the reaction (lane 7) while DTT had no effect (lane 6).

Nucleotidylylation of VPg was specific as it was limited to UTP and poly(A). None of the other three ribonucleoside triphosphates was able to replace UTP, regardless of the template used [poly(G), poly(C), or poly(U)] and no label was transferred to VPg from [$\gamma^{32}P$]ATP. These findings indicate that the 3'-terminal poly (A) of the poliovirus genome (Yogo, Y., et al. (1972) *Proc. Natl. Acad. Sci. USA* 69, 1877–1882.) is the site where genome replication commences (Yogo, Y., et al. (1975) *J. Mol. Biol.* 92, 467–477; Dorsch-Haesler, K. et al. (1975) *J. Virol.* 16, 1512–1517; Nomoto, A., et al. (1977) *Nature* 268, 208–213. Wimmer, E. (1982) *Cell* 28, 199–201.)

The yield of VPgpU(pU) was proportional to the concentration of the precursor, but higher molecular weight products indicative of transcription of the poly(A) template were not apparent (FIG. 1*a*, lanes 1–6). Polymers were synthesized, however, when the UTP concentration was increased to >10 μl (FIG. 1*a*, lanes 10–12; FIG. 2, lanes 3–5) and their synthesis was strictly dependent upon the presence of VPg (FIG. 2, lanes 6,7). Analyses of the homopolymeric RNA product formed in the elongation reaction revealed chains of varying length (FIG. 3, lane 1). The RNA product was partially hybridized to the poly(A) template as it was found to be partially sensitive to either of the single-strand specific RNases A or T2, or to double-strand specific RNase V1, but it was completely digested with mixtures of RNases (A/V1) (FIG. 3, lane 3) or T2/V1. After removal of VPgpU (pU) from the reaction mixture (FIG. 3, lane 1), treatment of the homopolymer (VPg-poly(U) with RNases A/V1 yielded VPgpUp (lane 3) that, in turn, was cleaved to VPgpU with alkaline phosphatase (lane 4).

Phosphorimager analysis revealed the expected values of 1% and 0.5% of the total label in VPgpUp and VPgpU, respectively. This finding confirmed that all homopolymer chains are linked to VPg.

Neither uridylylation nor elongation was effected by 0.1% non-ionic detergent NP40. However, the yield of products in a standard reaction was low, reflecting values reported for a similar nucleotidylylation reaction of phage ϕ 29 terminal protein by the phage-specific DNA polymerase. Blanco, L., et al. (1985) *Proc. Natl. Acad. Sci. USA* 82, 5325–5329. Esteban, J. A., et al. (1992) *Biochemistry* 31, 350–359. The reason for the low yield of VPgpU(pU) or VPg-poly(U) is not known. It is likely that efficient uridylylation may require additional specific viral or cellular factors, and/or a hydrophobic (membranous) environment to stabilize protein/RNA complexes.

Poliovirus $3D^{pol}$ oligomerizes with increasing molar concentration, thereby improving its ability to bind to RNA and use RNA primers to initiate RNA synthesis. Pata, J. D., et al. (1995) *RNA* 1, 466–477. Uridylylation and elongation are optimal at 1 μM $3D^{pol}$ (FIGS. 4*a, b*), a concentration similar to that described for oligomerization of the enzyme. Pata, J. D., et al. (1995). Whether $3D^{pol}$ must form dimers to interact with VPg/poly(A) is not yet known.

$3D^{pol}$ is an exceptional RNA polymerase because it is strictly primer dependent (Flanegan, J. B., et al. (1977); Paul, A. V., et al. (1994) *J. Biol. Chem.* 269, 29173–29181) as are all known DNA polymerases. A standard assay for $3D^{pol}$ activity is the transcription of poly(A) in the presence of oligo(U) or oligo$(dT)_{15}$ primers. Flanegan, J. B., et al. (1977); Paul, A. V., et al. (1994). Comparison of the priming ability of VPg, VPgpU(Dreef-Tromp, C. M., et al., 1992 *Nuc. Acids. Res.* 20:2435–2439), and oligo$(dT)_{15}$ at different $3D^{pol}$ concentrations reveal that the oligonucleotide was far superior to the protein primers (FIG. 4*c* and legend). Yet all three reactions were optimal at roughly the same enzyme concentration (FIG. 4*c*). This difference is likely due to the high efficiency with which the oligo$(dT)_{15}$ primer will bind to any part of the poly(A) template. [$^3$H-uracil] UTP was used in these experiments as substrate to confirm that the resulting polymer was indeed VPg-poly(U).

EXAMPLE 3

The experiments detailed in Example 2 were repeated with a genetic variant of $3D^{pol}$ to exclude the possibility that the uridylylation/elongation reactions might have been catalyzed by contaminating activities that accidentally co-purified with the recombinant $3D^{pol}$ from *E. coli* cells. A M394T mutation in $3D^{pol}$ has been shown to confer a ts phenotype to poliovirus replication, specifically to the initiation of minus strand RNA synthesis in vivo and in vitro. Barton, D. J., et al. (1996) *Virology* 217, 459–469. Purified M394T-$3D^{pol}$, obtained from J. Lyle and K. Kirkegaard, was able to catalyze uridylylation and elongation at 30° C. albeit with reduced activity when compared to wt $3D^{pol}$ (FIG. 5). At 36° C., however, M394T-$3D^{pol}$ was essentially inactive (<7%) in both reactions (FIG. 5*b*). This interesting result indicates that the ts phenotype of the poliovirus M394T-$3D^{pol}$ mutant (Barton, D. J., et al. (1996)) is related to a defect in VPg uridylylation at the non-permissive temperature.

Both uridylylation and elongation were completely inhibited by 15 μM gliotoxin, a fungal metabolite shown previously to inhibit poliovirus RNA replication in vivo and oligo(U)-primed poly(U) synthesis in vitro by purified $3D^{pol}$. Rodriguez, P. L. et al. (1992) *J. Virol.* 66, 1971–1976. Together these data prove that $3D^{pol}$ is the activity that catalyzes uridylylation/elongation of VPg.

Experiments carried out with sequence variants of VPg confirmed that the bond between VPg and nucleotide in VPgpU(pU) is $O^4$-(5'-uridylyl)tyrosine. Rothberg, P. G., et al. (1978); Ambros, V., et al. (1978); Cao, X., and Wimmer, E. 1995 *Virology* 209:315–326 Kuhn, R. J., et al. (1988) *Proc. Natl. Acad. Sci. USA* 85, 519–523. No product was formed with VPg(Y3F), as was expected (FIG. 6*a*, lanes 2–4). Moreover, VPg(Y3F) failed to generate VPg-poly(U) (FIG. 6*d*, lane 4). This observation demonstrated that elongation is dependent on functioning VPg. It has been observed previously that a poliovirus VPg(T4A) mutant has expressed a growth phenotype (Cao, X., and Wimmer, E. (1995)), a genetic defect that correlated with inefficient uridylylation of VPg(T4A) in a standard reaction (FIG. 6*b*, lanes 3–5). Testing a VPg(R17E) variant was of particular interest since changes of the arginine in this position to different amino acids (R17E, R17Q, R17K) have been shown to be lethal to poliovirus. Kuhn, R. J. et al. (1988) *Proc. Natl. Acad. Sci. USA* 85, 519–523; Xiang, W., et al. (1995) *RNA* 1, 892–904. Remarkably, VPg(R17E) did not serve as substrate either for uridylylation (FIG. 6*c*, lanes 3–5) or for elongation (data not shown). Both non-reactive variants (Y3F and R17E) interfered with the uridylylation reaction of wt VPg but only at relatively high concentrations (FIGS. 6*a, c*, lanes 5–7 and 6–8, respectively).

The foregoing data describes a mechanism of protein-primed initiation of poliovirus genome replication that explains numerous biochemical and genetic data published previously. Takegami, T., et al. (1983; Takeda, N., et al. (1986); Toyoda, H., et al. (1987); Yogo, Y., et al. (1972); Yogo, Y., et al. (1975); Dorsch-Haesler, K. et al. (1975); Nomoto, A., et al.; Wimmer, E. (1982).

EXAMPLE 4

In Vitro Assay 1. The reaction mixture (20 μl) contained 50 mM Hepes buffer pH 7.5, 0.5 mM manganous acetate, 6% glycerol, 0.5 μg poly(A) (200 nt), 1 μg purified poliovirus RNA polymerase, 0.5–1 μC of [$^{32}$P]-UTP, 0.1 μM UTP and 2 μg of synthetic poliovirus VPg. The mixture was incubated at 33° C. for one hour and the products analyzed on a 13.5% acrylamide-Tris/Tricine/SDS gel. Results indicated that under these conditions, poliovirus RNA polymerase $3D^{pol}$ uridylylates VPg in the presence of UTP and a poly(A) template (FIG. 1*b*).

The preferred assay conditions, resulting in optimal yield of reaction products, are described above. However, the reactions can be detected over a wide range of assay conditions, resulting in lower yields of products VPgpU(pU) and VPg-poly(U). When magnesium acetate (3.5 mM) is used in the assay instead of manganous acetate, the yield of reactions products decreases 100 fold. In contrast, the use of cobaltous acetate or zinc acetate, instead of manganous acetate leads to a 5 and 10 fold decrease, respectively, in the yield of the same products.

EXAMPLE 5

In Vitro Assay 2.

The reaction mixture (20 μl) contained 50 mM Hepes buffer pH 7.5, 3.5 mM Magnesium acetate 6% glycerol, 0.5 μg of purified transcript RNA consisting of poliovirus plus strand sequence having nucleotides 4435–4502 of FIG. 8 (SEQ ID NO:1), 1 μg purified polio RNA polymerase, 1.2 μg of purified poliovirus protein $3CD^{pro}$, 1 μC of [$^{32}$P]-UTP, 0.1 μM UTP and 2 μg of synthetic poliovirus VPg.

$3CD^{pro}$ was obtained by subcloning the relevant coding sequence from the poliovirus cDNA (ATCC Accession No. 45149) and expressing the protein in *E. coli*. Purification of $3CD^{pro}$ was by standard methods.

The mixture was incubated at 33° C. for one hour and the products analyzed on a 13.5% acrylamide-Tris/Tricine/SDS gel. As shown in FIG. 9, PVcre(2C) RNA serves as an excellent template for the uridylylation of VPg by $3D^{pol}$ (lane 1).

The same reaction was repeated using PVcre(2C) mutants in place of the wild type RNA template. Mutations were introduced into PVcre(2C) RNA by PCR mutagenesis using standard methods. Specific mutations introduced into PVcre (2C) are illustrated in FIG. 8 in bold type after the arrow heads.

Analysis of uridylylation products demonstrated that mutations within this loop and also in the stem of this structure either reduce (M2 in lane2, M3 in lane 4) or abolish (M1 in lane 2, M4 in lane 5) the synthesis of VPgpU(pU) in this assay.

The in vitro uridylylation reaction on the RNA hairpin, also called cre(2C), or cis replicating element in protein $2C^{ATPase}$, is strongly stimulated by another viral protein, $3CD^{pro}$ (FIG. 10). Genetic analysis with mutants of the cre(2C) RNA hairpin indicates that in vitro, the uridylylation of VPg occurs on the small loop of the hairpin that contains the AMP-rich AAACA sequence (FIG. 9).

The stimulation of VPgpU(pU) by $3D^{pol}$ is particularly evident when magnesium acetate is used as a cofactor for $3D^{pol}$. (FIG. 10, compare lanes 1 and 2). The stimulation of the reaction is less striking when manganous acetate is used in the assay (FIG. 10, compare lanes 3 and 4).

EXAMPLE 6

The in vitro assay described in Example 4 was repeated using Rhinovirus 2 RNA polymerase and Rhinovirus 2 VPg instead of poliovirus RNA polymerase and poliovirus VPg. The Rhinovirus cDNA was contained in the plasmid pGEX-HRV2-3D. pGEX-HRV2-3D was constructed by inserting the 3D polymerase gene from Rhinovirus 2 into pGEX-2T (Pharmacia). The 3D polymerase gene was subcloned from the HRV2 cDNA using well known methods. HRV2 cDNA was obtained from Dr. E. Kuechler (Duechler, M. et al., 1989 *Virology* 168:159–161).

HRV2 3D polymerase was expressed in *E. coli* as a GST fusion protein and was purified with Glutathione Sepharose 4B beads (Pharmacia Biotech) following directions of the manufacturer.

Reaction products were analyzed on a 13.5% acrylamide-Tris/Tricine/SDS gel. Results of the assay indicated that under the assay conditions, Rhinovirus RNA polymerase HRV2 3D uridylylates VPg in the presence of UTP and a poly(A) template.

EXAMPLE 7

In vitro Assay II (Example 5) was repeated using a portion of Rhinovirus 14 plus strand (nucleotides 2318–2413) as template rather than the poliovirus plus strand sequence. The HRV14RNA template used in the reaction had the following sequence:

```
5' UCA CUC ACU GAA GGC UUA GGU GAU GAA UUA
   GAA GAA GUC AUC GUU GAG AAA ACG AAA CAG ACG GUG GCC
   UCA AUC UCA UCU GGU CCA AAA CAC ACA 3'
```

and is also set forth in SEQ ID NO:2.

This particular sequence was chosen as it falls within the HRV14 RNA hairpin (McKnight, K., and Lemon, S. M. 1996 *J. Virol.* 70:1941–1952). Poliovirus RNA polymerase and poliovirus protein $3CD^{pro}$ used in the reaction were as described in Example 5.

Results indicated that HRV14 RNA sequence serves as an excellent template for the uridylylation of VPg by $3D^{pol}$.

TABLE 1

| (SEQ ID NOS: 3–43) | |
|---|---|
| Enterovirus VPg: | |
| PV1m | GAYTGL.PNkkPnVPTiRtAKVQ |
| PV1s | GAYTGL.PNkkPnVPTiRtAKVQ |
| PV2la | GAYTGL.PNkrPnVPTiRtAKVQ |
| PV2w2 | GAYTGL.PNkrPnVPTiRtAKVQ |
| PV2s | GAYTGL.PNkrPnVPTiRtAKVQ |
| PV3le | GAYTGL.PNkrPnVPTiRaAKVQ |
| PV3f | GAYTGL.PNkrPnVPTiRtAKVQ |
| PV3s | GAYTGL.PNkrPnVPTiRaAKVQ |
| ECHO6 | GAYTGM.PNqkPkVPTlRqAKVQ |
| ECHO11 | GAYTGM.PNqkPkVPTlRqAKVQ |
| ECHO12 | GAYTGM.PNqkPkVPTlRqAKVQ |
| EV70a | GpYTGL.PNqkPkVPTlRtAKVQ |
| EV70b | GpYTGL.PNqkPkVPTlRtAKVQ |
| EV71 | GAYsGa.PNqvlkkPvlRtAtVQ |
| CA9 | GAYTGi.PNqkPkVPTlRqAKVQ |
| CA16 | GAYsGa.PkqtlkkPilRtAtVQ |
| CA21 | GAYTGL.PNkkPnVPTiRiAKVQ |
| CA24 | GAYTGL.PNkkPsVPTvRtAKVQ |
| CB1 | GAYTGM.PNqkPkVPTlRqAKVQ |
| CB3a | GAYTGv.PNqkPrVPTlRqAKVQ |
| CB3b | GAYTGv.PNqkPrVPTlRqAKVQ |
| CB4a | GAYTGM.PNqkPkVPTlRqAKVQ |
| CB5 | GAYTGM.PNqkPkVPTlRqAKVQ |
| BEV1m4 | GpYsGvgtNyatkkPvvRqvqtQ |
| BEV1vg | GpYsGigtNyatkkPvvRqvqtQ |
| SVDukg | GAYTGM.PNqkPrVPTlRqAKVQ |
| SVDjl | GAYTGM.PNqkPkVPTlRqAKVQ |
| SVDh3 | GAYTGM.PNqkPkVPTlRqAKVQ |
| Consensus | GaYtGl-pnxkpkvPtlRqakvQ |
| Rhinovirus VPg: | |
| Rhino1a | GPYSGE.PKPKTKVPE.RRIVAQ |
| Rhino1b | GPYSGE.PKPKTKMPE.RRVVAQ |
| Rhino2 | GPYSGE.PKPKTKIPE.RRVVtQ |
| Rhino9 | GPYSGE.PKPKTRVPE.RRVVAQ |
| Rhino14 | GPYSGnpPhnKlKaPtlRpVVvQ |
| Rhino16 | GPYSGE.PKPKTKVPE.RRVVAQ |
| Rhino85 | GPYSGE.PKPKTKIPE.RRVVAQ |
| Rhino89 | GPYSGE.PKPKsRaPE.RRVVtQ |
| Consensus | GPYSGE-PKPKTKVPE-RRVVAQ |

TABLE 1-continued

| (SEQ ID NOS: 3–43) | |
|---|---|
| Other picornavirus VPgs: | |
| SVDV | GAYTGM PNQKPKVPTLRQAKVQ |
| HAV | GVYHGVTKPKQVJKLDADP..VE |
| FMDV | GPYTGPLERQRPLKVRAKLPQQE |

TABLE 2

The family *Picornaviridae*[a]

| Genus | Number of serotypes | Members |
|---|---|---|
| Rhinovirus | 102 | Human rhinoviruses 1A–100, 1B, "Hanks" |
| | 3 | Bovine rhinoviruses 1,2,3 |
| Enterovirus | 3 | Human polioviruses 1,2,3 |
| | 23 | Human Coxsackieviruses A1–22,24 (A23-echovirus 9)[b] |
| | 6 | Human Coxsackieviruses B1–6[c] (swine vesicular disease virus is very similar to coxsackie B5 virus) |
| | 30 | Human echoviruses 1–7,9,11–27,29–34<br>Echo 8 is echo 1[b]<br>Echo 10 is reovirus, type 1[b,d]<br>Echo 28 is human rhinovirus 1A[b] |
| | 4 | Human enteroviruses 68–71 |
| | 1 | Vilyuisk virus |
| | 18 | Simian enteroviruses 1–18 |
| | 2 | Bovine enteroviruses 1,2 |
| | 8 | Porcine enteroviruses 1–8 |
| Aphthovirus | 7 | Foot-and-mouth disease virus 1–7 (serotypes A,C,O,SAT-1,2,3,Asia-1) |
| Cardiovirus | 2 | Encephalomyocarditis (EMC) virus[e], Theiler's murine encephalomyelitis (TME) virus (TO, GDVII) |
| Hepatovirus | 1 | Human hepatitis virus A[f] |
| Unassigned | 3 | Equine rhinoviruses 1,2, cricket paralysis virus, *Drosophila* C virus |

[a]The so-called feline picornaviruses are now classified in the family *Caliciviridae.*

[b]Vacated numbers are now unused; Echovirus 22 is atypical in that it shows little sequence relationship to other picornaviruses (189).

[c]Coxsackieviruses are named after Coxsackie, New York, the town from which the initial isolates were made.

[d]Echo is an acronym for enteric cytopathic human orphan (274).

[e]Also mengovirus, Maus Eiberfeld (ME) virus, Columbia SK virus, MM virus.

[f]Formerly classified human enterovirus 72.

TABLE 3

RNA viruses with genome-linked protein (VPg)

| Virus group | Virus | Genome[a] | VPg, size | Linkage | Refs. |
|---|---|---|---|---|---|
| Picornavirus | Poliovirus | ssRNA | 22 aa | Tyr-pU | (280–287) |
| | Encephalomyocarditis virus | ssRNA | ~10,000 and 8,000 | Tyr-pU | (308, 309) |
| | Foot and mouth disease virus | ssRNA | 24, 25, and 26 aa | Tyr-pU | (311–315) |
| | Hepatitis A | ssRNA | 21–23 aa | Tyr-pU? | (316, 317) |
| Calicivirus | Vesicular exanthema virus | ssRNA | ~10,000 | nd | (318, 319) |
| — | Infectious pancreatic necrosis virus | dsRNA (2) | ~110,000 | nd | (320, 321) |
| — | Drosophila X Virus | dsRNA (2) | 67,000 | nd | (322, 323) |
| Comovirus | Cowpea mosaic virus | ssRNA (2) | 28 aa | Ser-pU | (324–327, 335) |
| | Radish mosaic virus | ssRNA (2) | nd | Ser-pN | (336) |
| | Squash mosaic virus | ssRNA (2) | nd | nd | (337) |
| | Etches Ackerbohn mosaic virus | ssRNA (2) | nd | nd | (337) |
| Luteovirus | Potato leafroll virus | ssRNA | ~7,000 | nd | (338) |
| | Barley yellow dwarf virus | ssRNA | ~17,000 | nd | (339) |
| Nepovirus | Tobacco ringspot virus | ssRNA (2) | ~4,000 | nd | (340–342) |
| | Tomato black ring virus | ssRNA (2) | ~6,000 | nd | (340,341,343) |
| | Arabis mosaic virus | ssRNA (2) | ~4,000 | nd | (344) |
| | Strawberry latent ringspot virus | ssRNA (2) | ~4,000 | nd | (344) |
| | Raspberry ringspot virus | ssRNA (2) | ~4,000 | nd | (344) |
| | Cherry leafroll virus | ssRNA (2) | ~3,500 | nd | (345) |
| Polyvirus | Tobacco etch virus | ssRNA | ~6,000 | nd | (346) |
| | Tobacco vein mottling virus | ssRNA | ~24,000 | nd | (347) |
| | Plum pox virus | ssRNA | ~20,000 | nd | (348) |
| Sobemovirus | Southern bean mosaic virus | ssRNA | ~12,000 | nd | (349, 350) |
| | Pea enation mosaic virus | ssRNA | ~17,000 | nd | (351) |

[a]The number of RNA molecules that compose the genome is indicated in parentheses when more than one molecule is present.

What is claimed is:

1. A method of identifying an inhibitor of picornaviral replication which comprises the steps of:

(a) incubating for a time and under conditions sufficient to detect uridylylation of picornaviral VPg a first reaction mixture comprising a buffer with an approximate pH of 7.0–8.0 and a buffer concentration of approximately 10–50 mM; a divalent metal in the form of at least one of approximately 0.1–0.5 mM manganous acetate, approximately 1–7 mM magnesium acetate, approximately 0.1–0.5 mM cobaltous acetate, or approximately 0.1–0.5 mM zinc acetate; approximately 2–10% glycerol; approximately 0.1–1.0 μg of poly(A); approximately 0.5–2.0 μg of purified picornaviral RNA polymerase; labeled UTP sufficient to identify labeled uridylylation reaction products; approximately 0.1–100 μM UTP; and approximately 0.5–5 μg of picornaviral VPg;

(b) incubating a second reaction mixture comprising the same reactants and under the same conditions as enumerated in step (a) with a potential inhibitor of picornaviral replication;

(c) comparing the level of uridylylation reaction products obtained in the first and second reaction mixtures; and (d) correlating a decrease in the level of uridylylation reaction products obtained in the second reaction mixture with the identification of an inhibitor of picornaviral RNA replication.

2. A method of identifying an inhibitor of picornaviral replication which comprises the steps of:

(a) incubating for a time and under conditions sufficient to detect uridylylation of picornaviral VPg a first reaction mixture comprising a buffer with an approximate pH of 7.0–8.0 and a buffer concentration of approximately 10–50 mM; a divalent metal in the form of at least one of approximately 0.1–0.5 mM manganous acetate, approximately 1–7 mM magnesium acetate, approximately 0.1–0.5 mM cobaltous acetate, or approximately 0.1–0.5 mM zinc acetate; approximately 2–10% glycerol; approximately 0.1–1.0 μg of purified picornaviral transcript corresponding to a an RNA hairpin structure located within the coding sequence of the picornavirus, approximately 0.5–2.0 μg of purified picornavirus RNA polymerase; approximately 0.2–1.2 μg of purified picornavirus protein $3CD^{pro}$; labeled UTP in an amount sufficient to detect uridylylated reaction products; 0.1–100 μM UTP and approximately 0.5–5.0 μg of picornaviral VPg;

(b) incubating a second reaction mixture comprising the same reactants and under the same conditions as enumerated in step (a) with a potential inhibitor of picornaviral replication;

(c) comparing the level of uridylylation reaction products obtained in the first and second reaction mixtures; and (e) correlating a decrease in the level of uridylylation reaction products obtained in the second reaction mixture with the identification of an inhibitor of picornaviral RNA replication.

3. The method of claim 1 or 2 wherein the potential inhibitor is at least one of a nucleotide analogue, a VPg analogue, a metal ion, or a randomly synthesized chemical.

4. The method of claim 1 or 2 wherein the labeled UTP is at least one of [$^{32}$P]-UTP, [$^{33}$P]-UTP, [$^{3}$H]-UTP or biotinylated UTP.

5. The method of claim 1 or 2 wherein the labeled UTP is [$^{32}$P]-UTP in an amount of approximately 0.5 to 10.0 $\mu$C.

6. The method of claim 1 or 2 wherein the reaction mixtures are incubated at a temperature in the range of from approximately 30° C. to approximately 37° C.

7. The method of claim 1 or 2 wherein the reaction mixtures are incubated for a time period in the range of from about five minutes to about several hours.

8. The method of claim 1 or 2 wherein the RNA polymerase is from poliovirus.

9. The method of claim 1 or 2 wherein the RNA polymerase is from Rhinovirus.

10. The method of claim 2 wherein the potential inhibitor is an oligonucleotide which is complementary to at least 8 nucleotides of a picornavirus RNA transcript having a hairpin loop within a coding region.

11. The method of claim 2 wherein the potential inhibitor is an oligonucleotide which is complementary to at least 10 nucleotides of the poliovirus plus strand sequence 4435–4502 as set forth in SEQ ID NO:1.

12. The method of claim 2 wherein the picornavirus transcript having an RNA hairpin structure in the coding sequence comprises an AMP rich sequence.

13. The method of claim 12 wherein the AMP rich sequence is AAACA.

* * * * *

SEQUENCE LISTING

```
<160> NUMBER OF SEQ ID NOS:  49

<210> SEQ ID NO 1
<211> LENGTH: 67
<212> TYPE: RNA
<213> ORGANISM: Unknown Organism
<220> FEATURE:
<223> OTHER INFORMATION: Description of Unknown Organism: rna poliovirus

<400> SEQUENCE: 1

gagcauacua uuaacaacua cauacaguuc aagagcaaac accguauuga accaguaugu     60

uugcuag                                                               67


<210> SEQ ID NO 2
<211> LENGTH: 96
<212> TYPE: RNA
<213> ORGANISM: Unknown Organism
<220> FEATURE:
<223> OTHER INFORMATION: Description of Unknown Organism: rhinovirus

<400> SEQUENCE: 2

ucacucacug aaggcuuagg ugaugaauua gaagaaguca ucguugagaa aacgaaacag     60

acgguggccu caaucucauc ugguccaaaa cacaca                               96


<210> SEQ ID NO 3
<211> LENGTH: 22
<212> TYPE: PRT
<213> ORGANISM: Unknown Organism
<220> FEATURE:
```

-continued

<223> OTHER INFORMATION: Description of Unknown Organism: Enterovirus

<400> SEQUENCE: 3

Gly Ala Tyr Thr Gly Leu Pro Asn Lys Lys Pro Asn Val Pro Thr Ile
1 5 10 15

Arg Thr Ala Lys Val Gln
20

<210> SEQ ID NO 4
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 4

Gly Ala Tyr Thr Gly Leu Pro Asn Lys Lys Pro Asn Val Pro Thr Ile
1 5 10 15

Arg Thr Ala Lys Val Gln
20

<210> SEQ ID NO 5
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 5

Gly Ala Tyr Thr Gly Leu Pro Asn Lys Arg Pro Asn Val Pro Thr Ile
1 5 10 15

Arg Thr Ala Lys Val Gln
20

<210> SEQ ID NO 6
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 6

Gly Ala Tyr Thr Gly Leu Pro Asn Lys Arg Pro Asn Val Pro Thr Ile
1 5 10 15

Arg Thr Ala Lys Val Gln
20

<210> SEQ ID NO 7
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 7

Gly Ala Tyr Thr Gly Leu Pro Asn Lys Arg Pro Asn Val Pro Thr Ile
1 5 10 15

Arg Thr Ala Lys Val Gln
20

<210> SEQ ID NO 8
<211> LENGTH: 22
<212> TYPE: PRT
<213> ORGANISM: Unknown Organism -continued
<220> FEATURE:
<223> OTHER INFORMATION: Description of Unknown Organism: Enterovirus

<400> SEQUENCE: 8

Gly Ala Tyr Thr Gly Leu Pro Asn Lys Arg Pro Asn Val Pro Thr Ile
1 5 10 15

Arg Ala Ala Lys Val Gln
20

<210> SEQ ID NO 9
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 9

Gly Ala Tyr Thr Gly Leu Pro Asn Lys Arg Pro Asn Val Pro Thr Ile
1 5 10 15

Arg Thr Ala Lys Val Gln
20

<210> SEQ ID NO 10
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 10

Gly Ala Tyr Thr Gly Leu Pro Asn Lys Arg Pro Asn Val Pro Thr Ile
1 5 10 15

Arg Ala Ala Lys Val Gln
20

<210> SEQ ID NO 11
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 11

Gly Ala Tyr Thr Gly Met Pro Asn Gln Lys Pro Lys Val Pro Thr Leu
1 5 10 15

Arg Gln Ala Lys Val Gln
20

<210> SEQ ID NO 12
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 12

Gly Ala Tyr Thr Gly Met Pro Asn Gln Lys Pro Lys Val Pro Thr Leu
1 5 10 15

Arg Gln Ala Lys Val Gln
20

<210> SEQ ID NO 13
<211> LENGTH: 22
<212> TYPE: PRT

-continued

<213> ORGANISM: Unknown Organism
<220> FEATURE:
<223> OTHER INFORMATION: Description of Unknown Organism: Enterovirus

<400> SEQUENCE: 13

Gly Ala Tyr Thr Gly Met Pro Asn Gln Lys Pro Lys Val Pro Thr Leu
1 5 10 15

Arg Gln Ala Lys Val Gln
20

<210> SEQ ID NO 14
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 14

Gly Pro Tyr Thr Gly Leu Pro Asn Gln Lys Pro Lys Val Pro Thr Leu
1 5 10 15

Arg Thr Ala Lys Val Gln
20

<210> SEQ ID NO 15
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 15

Gly Pro Tyr Thr Gly Leu Pro Asn Gln Lys Pro Lys Val Pro Thr Leu
1 5 10 15

Arg Thr Ala Lys Val Gln
20

<210> SEQ ID NO 16
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 16

Gly Ala Tyr Ser Gly Ala Pro Asn Gln Val Leu Lys Lys Pro Val Leu
1 5 10 15

Arg Thr Ala Thr Val Gln
20

<210> SEQ ID NO 17
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 17

Gly Ala Tyr Thr Gly Ile Pro Asn Gln Lys Pro Lys Val Pro Thr Leu
1 5 10 15

Arg Gln Ala Lys Val Gln
20

<210> SEQ ID NO 18
<211> LENGTH: 22

-continued

<212> TYPE: PRT
<213> ORGANISM: Unknown Organism
<220> FEATURE:
<223> OTHER INFORMATION: Description of Unknown Organism: Enterovirus

<400> SEQUENCE: 18

Gly Ala Tyr Ser Gly Ala Pro Lys Gln Thr Leu Lys Lys Pro Ile Leu
1 5 10 15

Arg Thr Ala Thr Val Gln
20

<210> SEQ ID NO 19
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 19

Gly Ala Tyr Thr Gly Leu Pro Asn Lys Lys Pro Asn Val Pro Thr Ile
1 5 10 15

Arg Ile Ala Lys Val Gln
20

<210> SEQ ID NO 20
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 20

Gly Ala Tyr Thr Gly Leu Pro Asn Lys Lys Pro Ser Val Pro Thr Val
1 5 10 15

Arg Thr Ala Lys Val Gln
20

<210> SEQ ID NO 21
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 21

Gly Ala Tyr Thr Gly Met Pro Asn Gln Lys Pro Lys Val Pro Thr Leu
1 5 10 15

Arg Gln Ala Lys Val Gln
20

<210> SEQ ID NO 22
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 22

Gly Ala Tyr Thr Gly Val Pro Asn Gln Lys Pro Arg Val Pro Thr Leu
1 5 10 15

Arg Gln Ala Lys Val Gln
20

<210> SEQ ID NO 23

-continued

<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 23

Gly Ala Tyr Thr Gly Val Pro Asn Gln Lys Pro Arg Val Pro Thr Leu
1 5 10 15

Arg Gln Ala Lys Val Gln
20

<210> SEQ ID NO 24
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 24

Gly Ala Tyr Thr Gly Met Pro Asn Gln Lys Pro Lys Val Pro Thr Leu
1 5 10 15

Arg Gln Ala Lys Val Gln
20

<210> SEQ ID NO 25
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 25

Gly Ala Tyr Thr Gly Met Pro Asn Gln Lys Pro Lys Val Pro Thr Leu
1 5 10 15

Arg Gln Ala Lys Val Gln
20

<210> SEQ ID NO 26
<211> LENGTH: 23
<212> TYPE: PRT
<213> ORGANISM: Unknown Organism
<220> FEATURE:
<223> OTHER INFORMATION: Description of Unknown Organism: Enterovirus

<400> SEQUENCE: 26

Gly Pro Tyr Ser Gly Val Gly Thr Asn Tyr Ala Thr Lys Lys Pro Val
1 5 10 15

Val Arg Gln Val Gln Thr Gln
20

<210> SEQ ID NO 27
<211> LENGTH: 23
<212> TYPE: PRT
<213> ORGANISM: Unknown Organism
<220> FEATURE:
<223> OTHER INFORMATION: Description of Unknown Organism: Enterovirus

<400> SEQUENCE: 27

Gly Pro Tyr Ser Gly Ile Gly Thr Asn Tyr Ala Thr Lys Lys Pro Val
1 5 10 15

Val Arg Gln Val Gln Thr Gln
20

-continued

<210> SEQ ID NO 28
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 28

```
Gly Ala Tyr Thr Gly Met Pro Asn Gln Lys Pro Arg Val Pro Thr Leu
  1               5                  10                  15

Arg Gln Ala Lys Val Gln
             20
```

<210> SEQ ID NO 29
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 29

```
Gly Ala Tyr Thr Gly Met Pro Asn Gln Lys Pro Lys Val Pro Thr Leu
  1               5                  10                  15

Arg Gln Ala Lys Val Gln
             20
```

<210> SEQ ID NO 30
<211> LENGTH: 22
<212> TYPE: PRT
<213> ORGANISM: Unknown Organism
<220> FEATURE:
<223> OTHER INFORMATION: Description of Unknown Organism: Enterovirus

<400> SEQUENCE: 30

```
Gly Ala Tyr Thr Gly Met Pro Asn Gln Lys Pro Lys Val Pro Thr Leu
  1               5                  10                  15

Arg Gln Ala Lys Val Gln
             20
```

<210> SEQ ID NO 31
<211> LENGTH: 22
<212> TYPE: PRT
<213> ORGANISM: Unknown Organism
<220> FEATURE:
<223> OTHER INFORMATION: Description of Unknown Organism: Enterovirus
<221> NAME/KEY: UNSURE
<222> LOCATION: 9
<223> OTHER INFORMATION: Xaa is any amino acid

<400> SEQUENCE: 31

```
Gly Ala Tyr Thr Gly Leu Pro Asn Xaa Lys Pro Lys Val Pro Thr Leu
  1               5                  10                  15

Arg Gln Ala Lys Val Gln
             20
```

<210> SEQ ID NO 32
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 32

```
Gly Pro Tyr Ser Gly Glu Pro Lys Pro Lys Thr Lys Val Pro Glu Arg
  1               5                  10                  15
```

-continued

```
Arg Ile Val Ala Gln
            20


<210> SEQ ID NO 33
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 33

Gly Pro Tyr Ser Gly Glu Pro Lys Pro Lys Thr Lys Met Pro Glu Arg
  1               5                  10                  15

Arg Val Val Ala Gln
            20


<210> SEQ ID NO 34
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 34

Gly Pro Tyr Ser Gly Glu Pro Lys Pro Lys Thr Lys Ile Pro Glu Arg
  1               5                  10                  15

Arg Val Val Thr Gln
            20


<210> SEQ ID NO 35
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 35

Gly Pro Tyr Ser Gly Glu Pro Lys Pro Lys Thr Arg Val Pro Glu Arg
  1               5                  10                  15

Arg Val Val Ala Gln
            20


<210> SEQ ID NO 36
<211> LENGTH: 23
<212> TYPE: PRT
<213> ORGANISM: Unknown Organism
<220> FEATURE:
<223> OTHER INFORMATION: Description of Unknown Organism: Rhinovirus

<400> SEQUENCE: 36

Gly Pro Tyr Ser Gly Asn Pro Pro His Asn Lys Leu Lys Ala Pro Thr
  1               5                  10                  15

Leu Arg Pro Val Val Val Gln
            20


<210> SEQ ID NO 37
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 37

Gly Pro Tyr Ser Gly Glu Pro Lys Pro Lys Thr Lys Val Pro Glu Arg
  1               5                  10                  15
```

-continued

Arg Val Val Ala Gln
20

<210> SEQ ID NO 38
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 38

Gly Pro Tyr Ser Gly Glu Pro Lys Pro Lys Thr Lys Ile Pro Glu Arg
1 5 10 15

Arg Val Val Ala Gln
20

<210> SEQ ID NO 39
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 39

Gly Pro Tyr Ser Gly Glu Pro Lys Pro Lys Ser Arg Ala Pro Glu Arg
1 5 10 15

Arg Val Val Thr Gln
20

<210> SEQ ID NO 40
<211> LENGTH: 21
<212> TYPE: PRT
<213> ORGANISM: Unknown Organism
<220> FEATURE:
<223> OTHER INFORMATION: Description of Unknown Organism: Rhinovirus

<400> SEQUENCE: 40

Gly Pro Tyr Ser Gly Glu Pro Lys Pro Lys Thr Lys Val Pro Glu Arg
1 5 10 15

Arg Val Val Ala Gln
20

<210> SEQ ID NO 41
<211> LENGTH: 22
<212> TYPE: PRT
<213> ORGANISM: Unknown Organism
<220> FEATURE:
<223> OTHER INFORMATION: Description of Unknown Organism: picornavirus

<400> SEQUENCE: 41

Gly Ala Tyr Thr Gly Met Pro Asn Gln Lys Pro Lys Val Pro Thr Leu
1 5 10 15

Arg Gln Ala Lys Val Gln
20

<210> SEQ ID NO 42
<211> LENGTH: 21
<212> TYPE: PRT
<213> ORGANISM: Unknown Organism
<220> FEATURE:
<223> OTHER INFORMATION: Description of Unknown Organism: picornavirus
<221> NAME/KEY: UNSURE
<222> LOCATION: 13
<223> OTHER INFORMATION: Xaa is any amino acid -continued

<400> SEQUENCE: 42

```
Gly Val Tyr His Gly Val Thr Lys Pro Lys Gln Val Xaa Lys Lys Asp
  1               5                  10                  15

Ala Asp Pro Val Glu
             20
```

<210> SEQ ID NO 43
<211> LENGTH: 23
<212> TYPE: PRT
<213> ORGANISM: Unknown Organism
<220> FEATURE:
<223> OTHER INFORMATION: Description of Unknown Organism: picornavirus

<400> SEQUENCE: 43

```
Gly Pro Tyr Thr Gly Pro Leu Glu Arg Gln Arg Pro Leu Lys Val Arg
  1               5                  10                  15

Ala Lys Leu Pro Gln Gln Glu
             20
```

<210> SEQ ID NO 44
<211> LENGTH: 22
<212> TYPE: PRT
<213> ORGANISM: Unknown Organism
<220> FEATURE:
<223> OTHER INFORMATION: Description of Unknown Organism: picornavirus

<400> SEQUENCE: 44

```
Gly Ala Tyr Thr Gly Leu Pro Asn Lys Lys Pro Asn Val Pro Thr Ile
  1               5                  10                  15

Arg Thr Ala Lys Val Gln
             20
```

<210> SEQ ID NO 45
<211> LENGTH: 22
<212> TYPE: PRT
<213> ORGANISM: Unknown Organism
<220> FEATURE:
<223> OTHER INFORMATION: Description of Unknown Organism: picornavirus

<400> SEQUENCE: 45

```
Gly Ala Phe Thr Gly Leu Pro Asn Lys Lys Pro Asn Val Pro Thr Ile
  1               5                  10                  15

Arg Thr Ala Lys Val Gln
             20
```

<210> SEQ ID NO 46
<211> LENGTH: 22
<212> TYPE: PRT
<213> ORGANISM: Unknown Organism
<220> FEATURE:
<223> OTHER INFORMATION: Description of Unknown Organism: Picornavirus

<400> SEQUENCE: 46

```
Gly Ala Tyr Ala Gly Leu Pro Asn Lys Lys Pro Asn Val Pro Thr Ile
  1               5                  10                  15

Arg Thr Ala Lys Val Gln
             20
```

<210> SEQ ID NO 47
<211> LENGTH: 22
<212> TYPE: PRT
<213> ORGANISM: Unknown Organism
<220> FEATURE:
<223> OTHER INFORMATION: Description of Unknown Organism: picornavirus -continued

```
<400> SEQUENCE: 47

Gly Ala Tyr Thr Gly Leu Pro Asn Lys Lys Pro Asn Val Pro Thr Ile
  1             5                  10                  15

Glu Thr Ala Lys Val Gln
             20


<210> SEQ ID NO 48
<211> LENGTH: 22
<212> TYPE: PRT
<213> ORGANISM: Unknown Organism
<220> FEATURE:
<223> OTHER INFORMATION: Description of Unknown Organism: Poliovirus

<400> SEQUENCE: 48

Gly Ala Tyr Thr Gly Leu Pro Asn Lys Lys Pro Asn Val Pro Thr Ile
  1             5                  10                  15

Arg Thr Ala Lys Val Gln
             20


<210> SEQ ID NO 49
<211> LENGTH: 69
<212> TYPE: RNA
<213> ORGANISM: Unknown Organism
<220> FEATURE:
<223> OTHER INFORMATION: Description of Unknown Organism: Poliovirus

<400> SEQUENCE: 49

ggcucgagca uacuauuaac uacauacagu ucaagagcaa acaccguauu gaacaguaug     60

uuuugcuag                                                             69
```